United States Patent
Dutta et al.

(10) Patent No.: US 6,990,491 B2
(45) Date of Patent: Jan. 24, 2006

(54) SYSTEM AND METHOD FOR ACCESSIBILITY DATA MAINTENANCE AND PRIVILEGE AUTHORIZATION

(75) Inventors: Rabindranath Dutta, Los Angeles, CA (US); John C. Hartley, Round Rock, TX (US); Richard Scott Schwerdtfeger, Round Rock, TX (US)

(73) Assignee: International Business Machines Corporation, Armonk, NY (US)

( * ) Notice: Subject to any disclaimer, the term of this patent is extended or adjusted under 35 U.S.C. 154(b) by 482 days.

(21) Appl. No.: 10/318,592

(22) Filed: Dec. 12, 2002

(65) Prior Publication Data

US 2004/0117370 A1    Jun. 17, 2004

(51) Int. Cl.
*G06F 17/30* (2006.01)

(52) U.S. Cl. .................. 707/9; 707/6; 707/8; 707/10; 707/203; 707/204

(58) Field of Classification Search ............... 340/5.53; 345/810; 707/100, 6, 8, 9, 10, 203, 204; 705/2; 713/165
See application file for complete search history.

(56) References Cited

U.S. PATENT DOCUMENTS

| | | | | |
|---|---|---|---|---|
| 5,721,904 A | * | 2/1998 | Ito et al. | 707/8 |
| 6,477,530 B1 | * | 11/2002 | Omata et al. | 707/9 |
| 6,741,987 B2 | * | 5/2004 | Ito | 707/6 |
| 6,874,085 B1 | * | 3/2005 | Koo et al. | 713/165 |
| 2001/0050610 A1 | * | 12/2001 | Gelston | 340/5.53 |
| 2002/0010772 A1 | * | 1/2002 | Kusano | 709/223 |
| 2002/0014950 A1 | * | 2/2002 | Ayala et al. | 340/5.6 |
| 2002/0158912 A1 | * | 10/2002 | O'Rourke | 345/810 |
| 2003/0154187 A1 | * | 8/2003 | Hayakawa et al. | 707/1 |
| 2003/0177132 A1 | * | 9/2003 | Thomas et al. | 707/100 |
| 2003/0191669 A1 | * | 10/2003 | Fitzgerald et al. | 705/2 |
| 2004/0215597 A1 | * | 10/2004 | Fitzgerald et al. | 707/1 |

FOREIGN PATENT DOCUMENTS

| | | |
|---|---|---|
| CN | 1291309 A | 4/2001 |
| CN | 1310418 A | 8/2001 |

* cited by examiner

*Primary Examiner*—Thuy N. Pardo
(74) *Attorney, Agent, or Firm*—Van Leeuwen & Van Leeuwen; Diana R. Gerhardt

(57) ABSTRACT

A system and method for data maintenance and privilege authorization is presented. An accessibility database server receives an accessibility record request from a requestor that includes a user identifier and a requestor identifier. The requestor identifier may correspond to a user, a healthcare practitioner server, an insurance server, a transcoding proxy server, a portal server, a web server, an advertisement server, or a service provider. The accessibility database server compares the accessibility record request with the requestor's access permission to determine whether the requestor has access corresponding to the particular request. If the requestor is authorized for the particular request, the accessibility database server processes the accessibility record request.

17 Claims, 27 Drawing Sheets

800 ⟶

Configuration

User ID: [12345]   Password: [*****]
         805 ⟶              808 ⟶

| Configure User Data | Format PCD | Synchronize PCD |
|---|---|---|
| 810 ⟶ | 815 ⟶ | 820 ⟶ |

User Data

User ID: [12345] ⟵ 830   Password: [*****] ⟵ 832

Content Presentation Preferences

Zoom (%) [150] ⟵ 835

Sharpen Image [No] ⟵ 840     Left Justify [No] ⟵ 855
Stop Animator [No] ⟵ 845     Mouse Over [No] ⟵ 860
Stop Flashing [Yes]          Remove Background [Yes] ⟵ 865
              ⟵ 850

Billing Information

Type          Number                    Expiration
[Visa]        [1234 5678 9012 1234]     [01/04]
870 ⟶                    ⟵ 875                 ⟵ 880

Insurance Information

Name                  Insurer ID
[ABC Insurall Co.]    [I76543]   ⟵ 890
885 ⟶

| Accessibility Permission Access | | | | | | |
|---|---|---|---|---|---|---|
| REQUESTOR | DATA ENTRY | | | DATA RETRIEVAL | | |
| | Accessblty. Type | Hlthcare Pract. ID | Accessblty. Privileges | Accessblty. Type | Hlthcare Pract. ID | Accessblty. Privileges |
| 905 User | | Permitted | | Permitted | Permitted | Permitted |
| 910 Hlthcare. Pract. | Permitted | | Permitted | Permitted | Permitted | Permitted |
| 915 Insurance Server | | | | | | Permitted |
| 920 Service Provider | | | | | | Permitted |
| 925 Ad Server/Portal | | | | Permitted | | |

| User Accessibility Record | | | | |
|---|---|---|---|---|
| User | Accessblty. Type | Hlthcare Pract. ID | Accessblty. Privileges | Privilege Expirations |
| 965 U12345 | impaired vision | P98765 | reduced glasses | none |
| | | | Handicap Parking | none |
| | broken leg | P54321 | free wheelchair | 05/02 |
| | | | reduced bus fair | 05/02 |
| | | | reduced medications | 05/02 |

| Policy Holder Look-up Table | | | | |
| --- | --- | --- | --- | --- |
| User ID | Accessibility Type | Accessibility Privileges | Claims Paid to Date | Last Accessibility Database Update |
| U12345 | broken leg | free bus fare | $120 | 04/02 |
|  |  | free wheelchair | $75 |  |
| U45678 | blind | 80% transcode coverage | $560 | 10/02 |

Advertisement Tracker

| Presentation Type | Ad. Identifier | Ad. Weighting | Times Provided | Hit Rate |
|---|---|---|---|---|
| Blind | B1 | 3 | 2,400 | 14% |
| | B2 | 5 | 6,000 | 24% |
| | B3 | 3 | 2,450 | 2% |
| | B4 | 1 | 600 | 65% |
| Seizures | S1 | 5 | 4,500 | 32% |
| | S2 | 2 | 1,200 | 15% |

Advertisement User Tracker

| User ID | Accessibility Type | Last AD Identifier | # of Ad's |
|---|---|---|---|
| U12345 | blind | B3 | 36 |
| U23456 | seizures | S6 | 53 |
| U34567 | deaf | L4 | 12 |

| Accounting Look-up Table | | | | | |
|---|---|---|---|---|---|
| User ID | Accessibility Type | Insurance Coverage | Insurance Server ID | User Billing | Address |
| U12345 | blind | 80% | I43215 | Bill Direct | 123 Lariat Ct. |
| U23456 | seizures | 100% | I54321 | Visa 3424344555 | 432 Long Dr. |
| U34567 | deaf | 50% | I65432 | Bill Direct | 438 Drive Cir. |

SYSTEM AND METHOD FOR ACCESSIBILITY DATA MAINTENANCE AND PRIVILEGE AUTHORIZATION

BACKGROUND OF THE INVENTION

1. Technical Field

The present invention relates in general to a system and method for accessibility data maintenance and privilege authorization. More particularly, the present invention relates to a system and method for managing an accessibility database which includes user accessibility data and providing the accessibility data to authorized requestors.

2. Description of the Related Art

Information technology has provided, and continues to provide, a seemingly unlimited amount of information to users. Using the Internet, a user is able to retrieve content corresponding to a particular subject from virtually anywhere around the world. However, this seemingly unlimited amount of information is not in a presentation form that is useful to many users. For example, "spoken" content or content in brail is useful to a blind user but written content is not useful.

A user with accessibility needs may build a functional system that converts a content's original presentation form into a presentation form useful to the user. Using the example described above, the blind user is able to build a functional system that converts written content into spoken content. However, problems of high costs, incompatibility, and the complexity of building such a system exclude many users from building a system. In addition, multiple content formats, markup languages, device capabilities, and network constraints also limits a user's ability to use a personal computer to convert a content's original presentation form into a presentation form useful to the user.

The worldwide migration of the Internet to deliver applications to end users and the spread of wireless communications are decreasing dependence on PC based applications. This migration creates an opportunity to make content available to a user in a useful presentation form by providing a central architectural point from which to transform (i.e. transcode) a content's presentation form. This central architecture may be in the form of a portal server where data is aggregated and possibly transcoded to produce content. It may also be in the form of a "transcoding gateway" such as a transcoding proxy server. The capacity to transform a content's presentation form makes information more usable to a broad range of users, including users with special needs. By using a portal server or intermediary server at the central architectural point, this server modifies the content's presentation form independent of a target operating system and browser. This reduces the installation costs and management costs of client-based accessibility solutions.

Industry and the U.S. government also recognize that content is not currently available to many users. Section 508 of the Federal Rehabilitation Act requires the U.S. government to purchase accessible information technology. As a result of Section 508, businesses that market to the U.S. government are modifying their information technology products and enhancing their web content in order for it to be more accessible to users. To make web content more readily accessible, accessibility transcoding services are emerging. A transcoding server, or "web intermediary", intercepts content requested by a user and modifies its original presentation form to a presentation form useful to the user. The content's original presentation form remains unmodified on the content's server.

Challenges arise, however, with the onset of providing accessibility services, such as content transcoding, over a computer network. Users are often provided with an accessibility identifier, such as a handicap parking placard, which authorizes them to use a particular accessibility service, such as parking in a handicap parking space. A challenge found with providing accessibility privileges over a computer network is identifying which users have accessibility privileges corresponding to their particular accessibility service request.

Additionally, a challenge arises in traditional accessibility service verification. For example, a user with a heart condition may be vacationing in a foreign city and misplaced his handicap parking placard. In this example, it is not obvious that the user is handicapped and the user may have to contact his primary doctor in order to receive another handicap parking placard which may take weeks to receive.

What is needed, therefore, is a system and method for maintaining an accessibility database which provides user accessibility data, such as accessibility privileges, that is accessible by accessibility service providers over a computer network.

SUMMARY

It has been discovered that the aforementioned challenges are resolved by using an accessibility database server to process accessibility data requests based on a requestor's access permission.

The accessibility database server receives an accessibility record request from a requestor. The accessibility record request includes a user identifier and a requestor identifier. The requestor identifier may correspond to a user, a healthcare practitioner server, an insurance server, a transcoding proxy server, a portal server, a web server, an advertisement server, or a service provider. The accessibility database server retrieves an accessibility database record corresponding to the user identifier from a local storage area.

The accessibility database server compares the accessibility record request with the requestor's access permission to determine whether the requestor has access corresponding to the particular request. For example, the requestor may be an insurance server requesting accessibility data corresponding to one of its policyholders. In this example, the accessibility database server validates that the insurance server has permission access to the user's accessibility data. If the requestor is not authorized for the particular request, the accessibility database server denies the requestor access.

On the other hand, if the requestor is authorized for the particular request, the accessibility database server processes the accessibility record request. If the requestor is a user, the accessibility database server authorizes the user to enter healthcare practitioner server identifier information as well as retrieve accessibility type information, healthcare practitioner server information, and accessibility privileges from the database record.

If the requestor is a healthcare practitioner server, the accessibility database server authorizes the healthcare practitioner server to enter accessibility type information and accessibility privileges, as well as retrieve accessibility type information, healthcare practitioner server information, and accessibility privileges from the database record.

If the requestor is an insurance server or service provider, the accessibility database server authorizes the requestor to retrieve accessibility privileges from the database record. If the requestor is an advertisement server, an intermediary server, a web server, or a portal server, the accessibility database server authorizes the requestor to retrieve accessibility type information from the database record.

The foregoing is a summary and thus contains, by necessity, simplifications, generalizations, and omissions of detail; consequently, those skilled in the art will appreciate that the summary is illustrative only and is not intended to be in any way limiting. Other aspects, inventive features, and advantages of the present invention, as defined solely by the claims, will become apparent in the non-limiting detailed description set forth below.

BRIEF DESCRIPTION OF THE DRAWINGS

The present invention may be better understood, and its numerous objects, features, and advantages made apparent to those skilled in the art by referencing the accompanying drawings. The use of the same reference symbols in different drawings indicates similar or identical items.

FIG. 8A shows a user interface window in which a user uses to configure user data;

FIG. 8B shows a user preferences interface window that a user uses to view and modify his user data;

FIG. 9A shows an accessibility permission look-up table that identifies access permissions for various requestors;

FIG. 9B shows a user accessibility record window which includes accessibility data corresponding to a user identifier;

FIG. 10 shows an insurance server's policy holder look-up table which includes information corresponding to policy holders;

FIG. 11A shows an advertisement tracker look-up table that an advertisement server uses to track advertisement metrics;

FIG. 11B shows a user advertisement tracker look-up table that an advertisement server uses to track user metrics;

FIG. 12 shows an accounting service look-up table which an accounting service uses to identify user payment options;

DETAILED DESCRIPTION

The following is intended to provide a detailed description of an example of the invention and should not be taken to be limiting of the invention itself. Rather, any number of variations may fall within the scope of the invention which is defined in the claims following the description.

Figure 1:
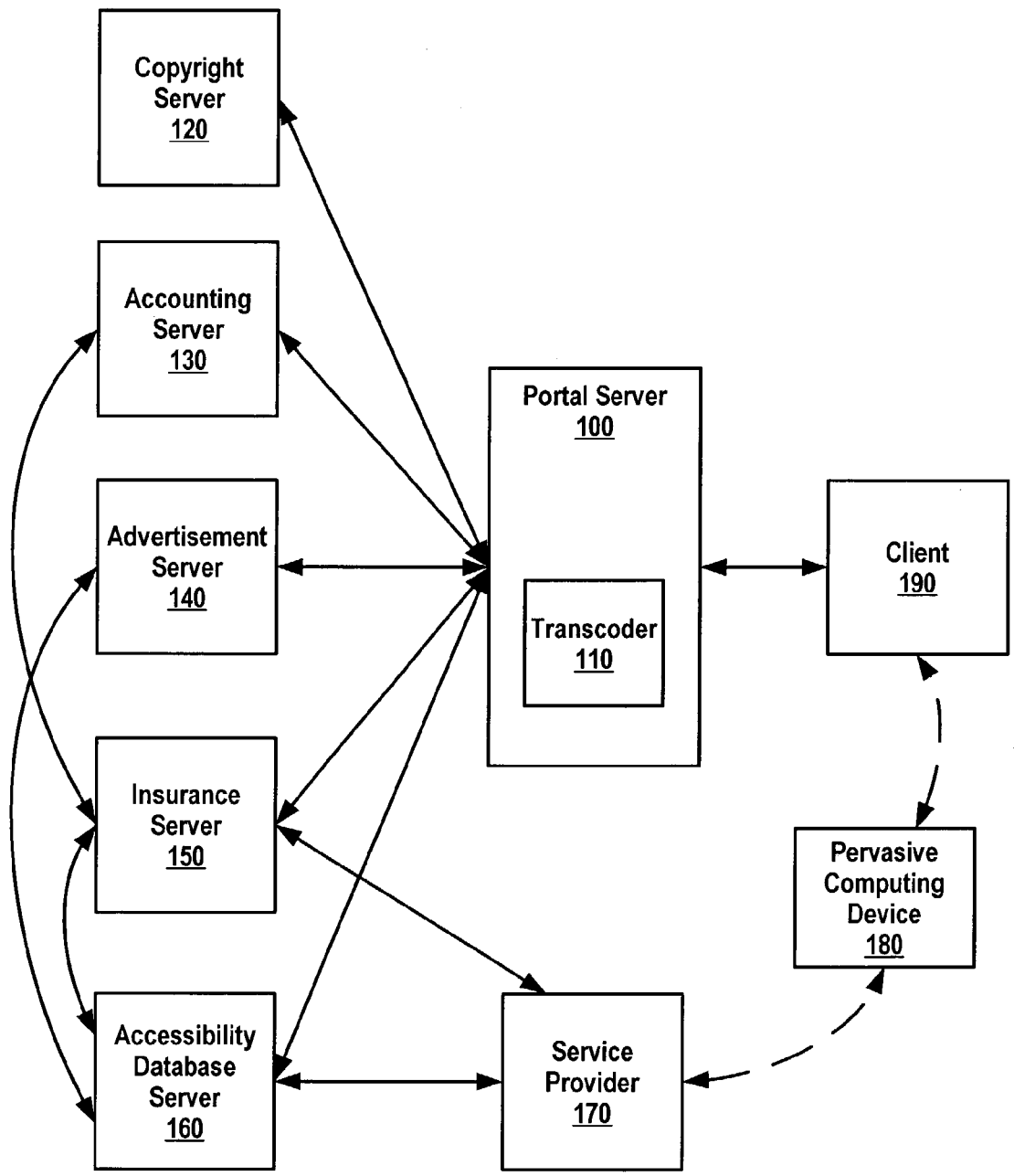
FIG. 1 is a high-level diagram showing computer servers processing a user request over a computer network.

FIG. 1 is a high-level diagram showing computer servers processing a user request over a computer network, such as the Internet. A user uses a pervasive computing device, such as pervasive computing device 180, to request content from a content provider. Pervasive computing device 180 provides user data to a client, such as client 190. Client 190 communicates with portal server 100 over a computer network, such as the Internet. Portal 100 may be used as a "hub" to process the user's content request, and communicate with various servers in order to process the user's request. The user's request includes a content transcoding request wherein the requested content is transcoded using transcoder 110. In one embodiment, a separate transcoding proxy server may perform the content transcoding function.

Portal server 100 communicates with copyright server 120 over a computer network, such as the Internet. When a requested content is copyright protected, copyright server 120 contacts the content owner to seek permission to transcode the content. The content owner may permit the content to be transcoded for free or for a transcoding fee. Copyright server 120 stores content transcoding permissions on a local storage area for future access (see FIGS. 3, 16, and corresponding text for further details regarding copyright server functions).

Portal server 100 communicates with accounting server 130 over a computer network, such as the Internet. Accounting server 130 tracks content transcoding events and manages account billings associated with the content transcoding events. Accounting server 130 may communicate with insurance server 150 to identify insurance coverage corresponding to a particular user that is requesting a content transcoding events (see FIGS. 3, 14, 15, and corresponding text for further details regarding accounting server functions).

Portal server 100 communicates with advertisement server 140 over a computer network, such as the Internet. Advertisement server 140 manages the distribution of transcoded advertisements to a user when the user requests content. Advertisement server 140 categorizes advertisements by presentation form and may selectively choose which advertisement to provide based upon the user and the user's preferences. Advertisement server 140 receives advertisements from one or more business servers and may provide the business servers with advertisement metric data (see FIGS. 2, 7, 17, and corresponding text for further details regarding advertisement server functions).

Portal server 100 communicates with insurance server 150 over a computer network, such as the Internet. Other servers, such as accounting services server 130 and accessibility database server 160, may communicate with insurance server 150 over a computer network, such as the Internet. Insurance server 150 receives a coverage request from a requestor corresponding to a particular user and verifies coverage information using the user's insurance policy information as well as what the user is requesting, such as a request to transcode content or a request for reduced bus fare (see FIGS. 3, 4, 18, 24, and corresponding text for further details regarding insurance server functions).

Portal server 100 communicates with accessibility database server 160 over a computer network, such as the Internet. Accessibility database server 160 manages an accessibility database which includes user accessibility data. Accessibility database server 160 receives requests from various requestors and provides information to the requestors based upon the requestors' access permission. Requestors, such as insurance server 150, advertisement server 140, and service provider 170, may access accessibility database server 160 over a computer network, such as the Internet (see FIGS. 2 through 6, 19 through 23, and corresponding text for further details regarding accessibility database server functions).

The user may also use his pervasive computing device, such as pervasive computing device 180, to request access to various services, such as handicap parking or reduced bus fare. Pervasive computing devices have an appearance as both traditionally computerized devices, such as desktop computers, tower computers, and portable computers, as well as newly computerized devices such as telephones, appliances, automobiles, and other devices, such as smartcards. Pervasive computing devices often include a system processor and associated volatile and non-volatile memory, a display area, input means, and often interfaces, such as a network interface or modem, to other computing devices.

The user invokes pervasive computing device 180 to communicate with service provider 170. For example, the user may insert pervasive computing device 180 in a slot located on service provider 170 if pervasive computing device 180 is a smartcard. Another example is the user may select a key sequence on pervasive computing device 180 to transmit information to service provider 170 over a wireless network if pervasive computing device 180 is a mobile phone. Service provider 170 may be a service provider server such as a parking garage server, a parking meter server, a public transportation server (i.e. bus fare service), an airport special assistance server i.e. wheelchair service), or another type of server that offers special assistance.

Figure 4:
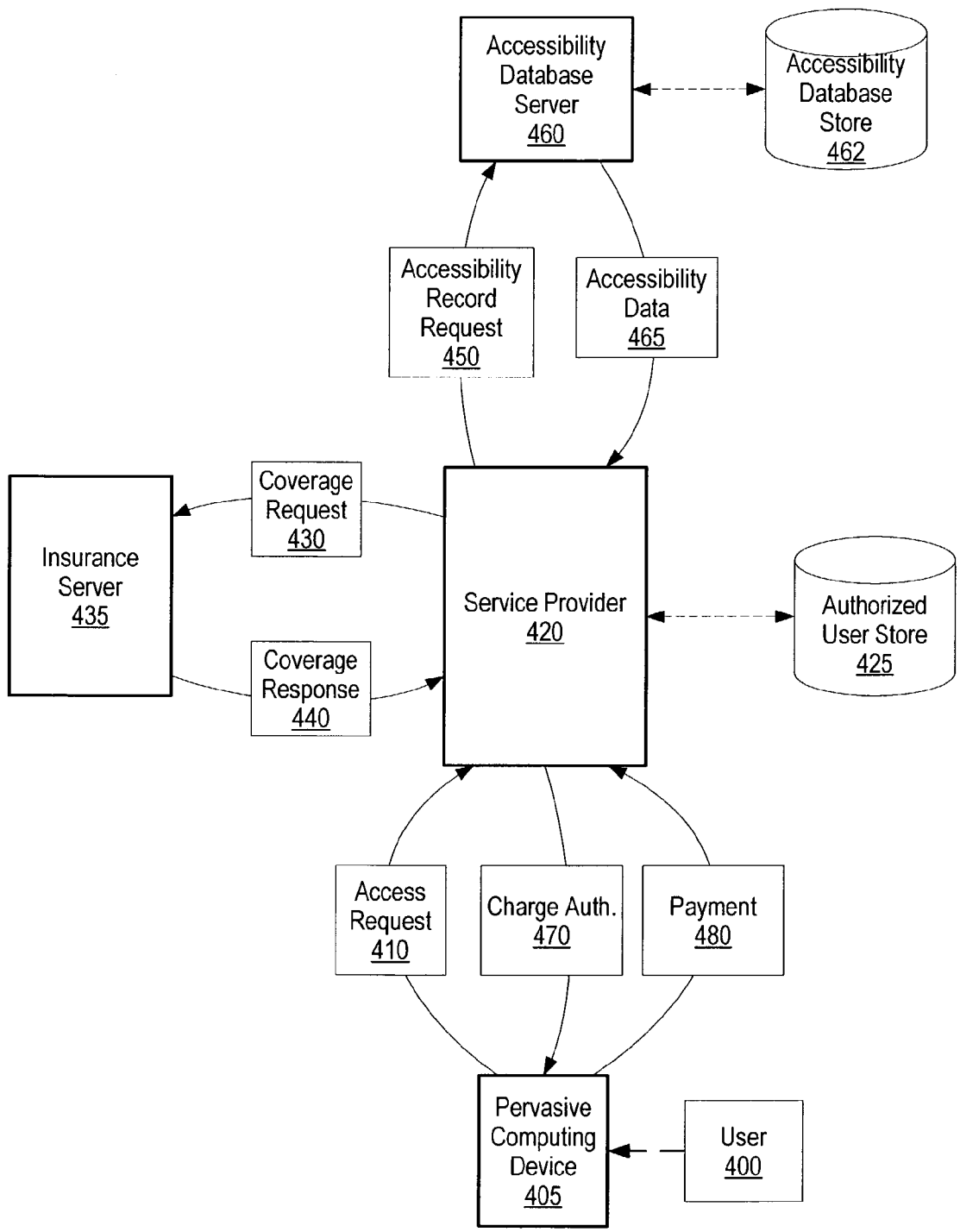
FIG. 4 is a diagram showing a user using a pervasive computing device to access a service.
Figure 23:
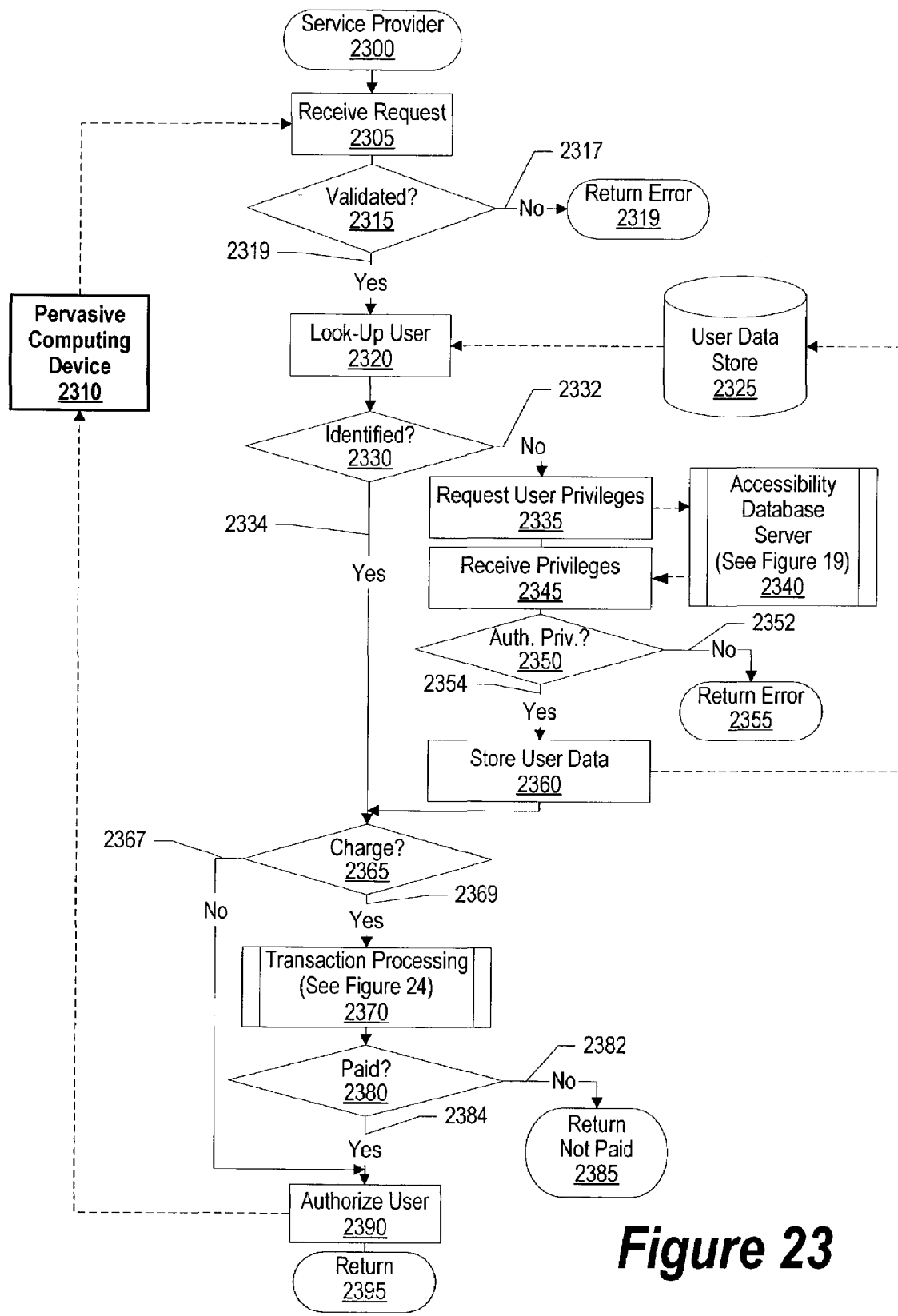
FIG. 23 is a flowchart showing steps taken in a service provider receiving a request from a user's pervasive computing device, processing the request, and authorizing the user.
Figure 24:
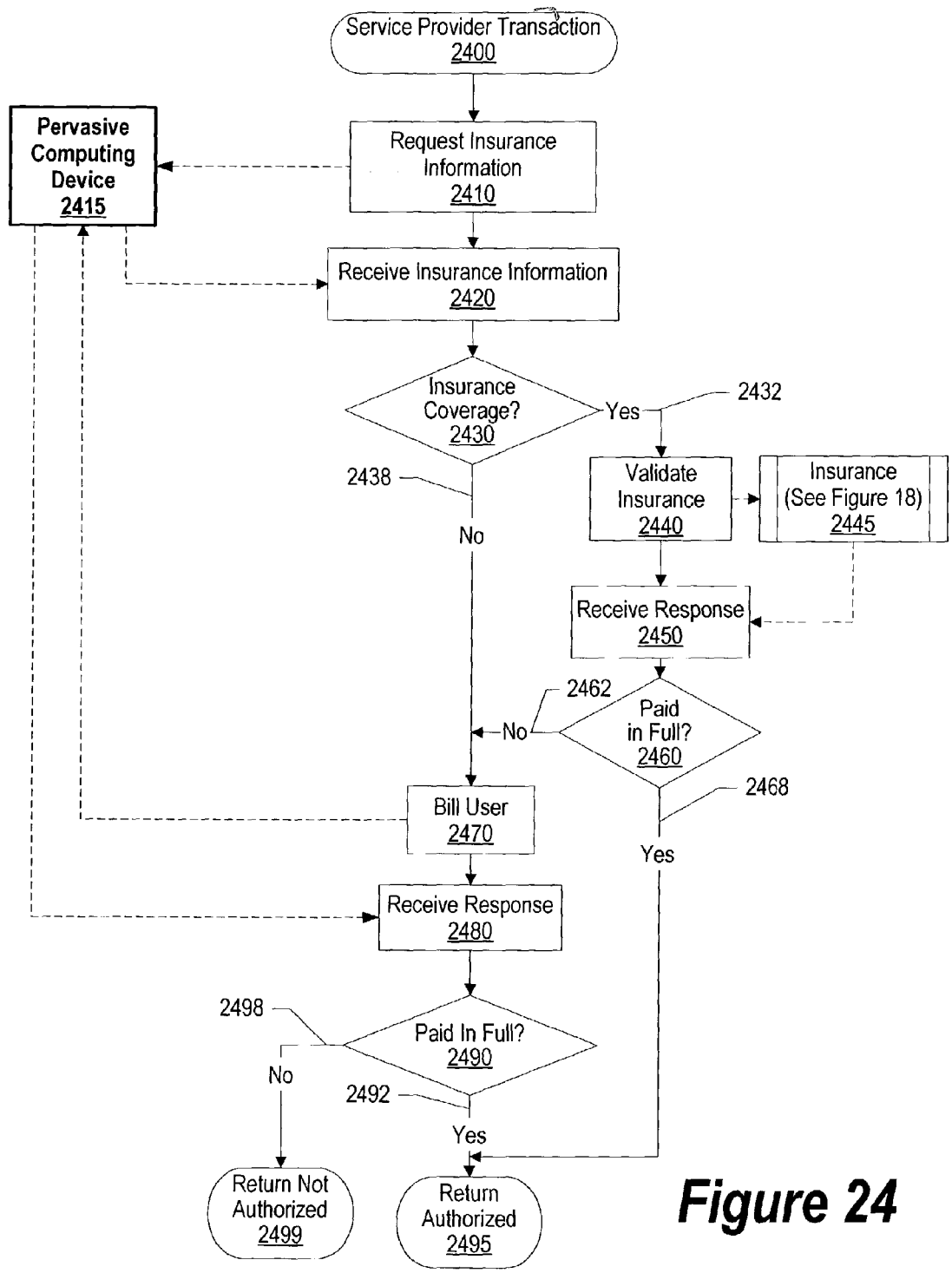
FIG. 24 is a flowchart showing steps taken in a service provider server processing a user transaction.

Service provider 170 receives the user's request, and may communicate with accessibility database server 160 and insurance server 150 to validate the user's access permissions and verify service fee payment if required (see FIGS. 4, 23, 24, and corresponding text for further details regarding user service requests).

Figure 2:
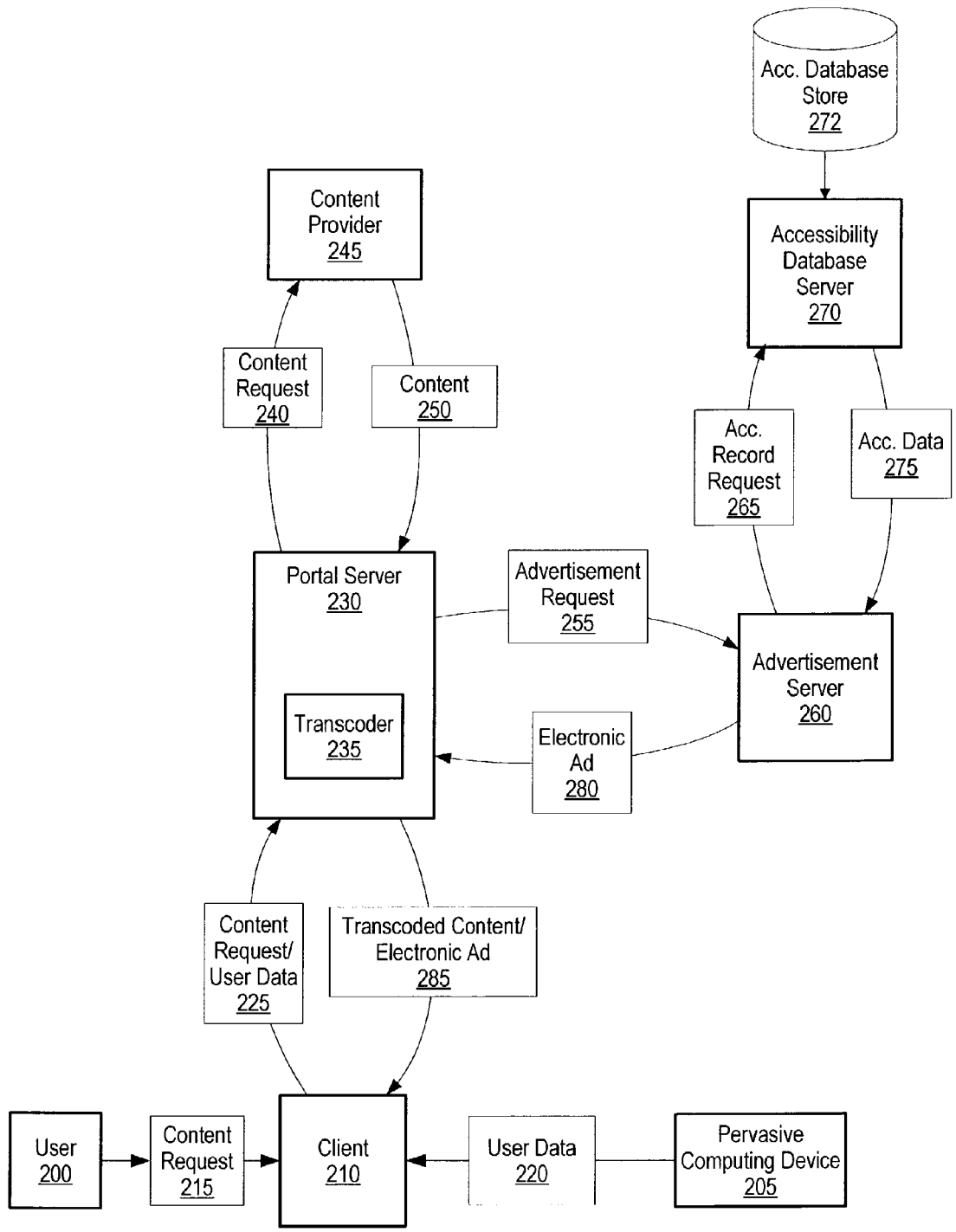
FIG. 2 is a diagram showing a user requesting content and receiving transcoded content along with an electronic advertisement.

FIG. 2 is a diagram showing a user requesting content and receiving transcoded content along with an electronic advertisement. User 200 sends content request 215 to a client, such as client 210. Content request 215 includes a request to transcode particular content, such as a web page. For example, user 200 may request to have a "sports" web page transcoded into "speech" and provided to him.

User 200 also uses pervasive computing device 205 to provide user data 220 to client 210. User data 220 includes information corresponding to user 200, such as a user identifier, accessibility types, content presentation preferences, and billing information.

Client 210 receives the content request and the user data, and sends content request/user data 225 to portal server 230 over a computer network, such as the Internet. Portal server 230 may be a third party server, such as Yahoo, that processes transcoding requests. Portal server 230 includes transcoder 235 which performs a content transcoding event. Using the example described above, transcoder 235 converts a sports web page into a "speech" file. In one embodiment, the content transcoding may occur separately from portal server 230 on a transcoding proxy server.

Portal server 230 receives content request/user data 225, separates the content request from the user data, and sends the content request, such as content request 240, to content provider 245. Using the example described above, portal server 230 identifies that the content request is directed to an ESPN server, and sends the content request to the ESPN server. Content provider 245 identifies the requested content, and sends content 250 to portal server 230. Using the example described above, content 250 may include batting average statistics for major league baseball players.

Portal server 230 analyzes user 200's user data received previously to determine how to transcode content 250 using transcoder 235. Using the example described above, transcoder 235 converts the batting average statistics into a "speech" file.

Portal server 230 sends advertisement request 255 to advertisement server 260 at any time while portal server 230 is processing content request/user data 225. For example, portal server 230 may send advertisement request 255 prior to sending content request 240 to content provider 245. Advertisement request 255 may include a presentation form which identifies a type of advertisement suitable for user 200. Using the example described above, the presentation form may specify a "spoken" advertisement. Advertisement request 255 may include user 200's user identifier in which advertisement server 260 uses to identify a suitable advertisement.

Figure 17:
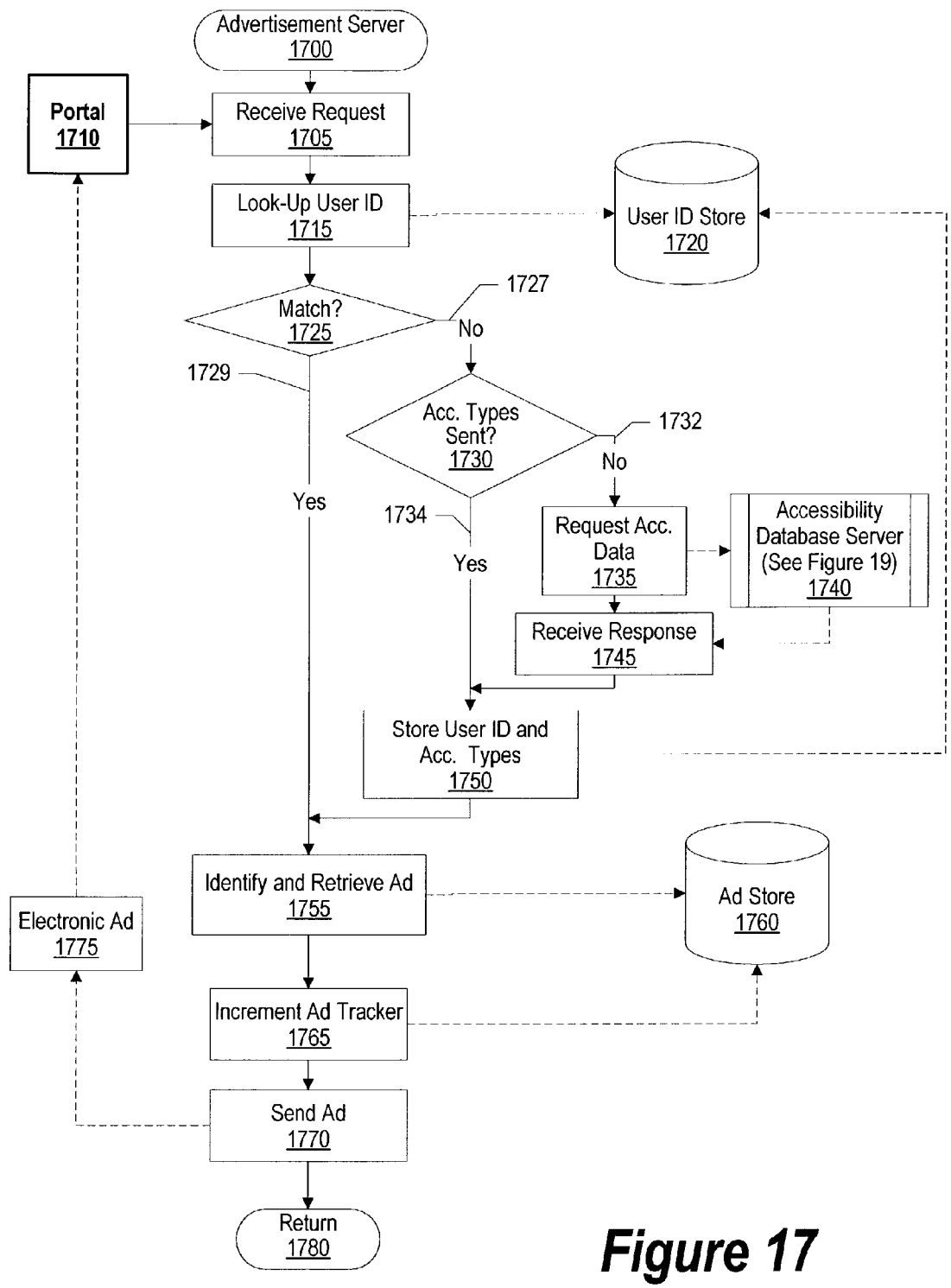
FIG. 17 is a flowchart showing an advertisement server receiving a request from a portal server or web server, identifying an electronic advertisement, and sending the electronic advertisement to the portal server or web server.

Advertisement server 260 receives advertisement request 255 and determines whether advertisement server 260 has enough information to identify which electronic advertisement to send to portal server 230 (see FIG. 17 and corresponding text for further details regarding advertisement selection). If advertisement server 260 determines that it requires more information regarding user 200's accessibility type, advertisement server 260 sends accessibility record request 265 to accessibility database server 270 through a computer network, such as the Internet.

Accessibility record request 265 includes advertisement server 260's advertisement server identifier as well as user 200's user identifier. Accessibility database provider 270 analyzes accessibility record request 265, retrieves accessibility data from accessibility database store 272, and sends accessibility data 275 to advertisement server 260. Accessibility data 275 includes accessibility data corresponding to user 200 in which advertisement server 260 is permitted access (see FIGS. 9A, 19, 22B, and corresponding text for further details regarding accessibility data access permission).

Advertisement server 260 identifies an electronic advertisement for user 200 using accessibility data 275, and sends electronic advertisement 280 to portal server 230. Portal server 230 combines the transcoded content with the electronic advertisement, and sends a transcoded content electronic advertisement response, such as transcoded content/electronic advertisement 285 to client 210. Using the example described above, the user listens to "spoken" batting average statistics and the "spoken" advertisement.

In one embodiment, portal server 230 may store electronic advertisements on a local storage device and associate electronic advertisements with user accessibility types. For example, portal server 230 may store "large font" advertisements on the local storage device, and retrieve one of the "large font" advertisements to send to a visually impaired user when the visually impaired user requests content.

Figure 3:
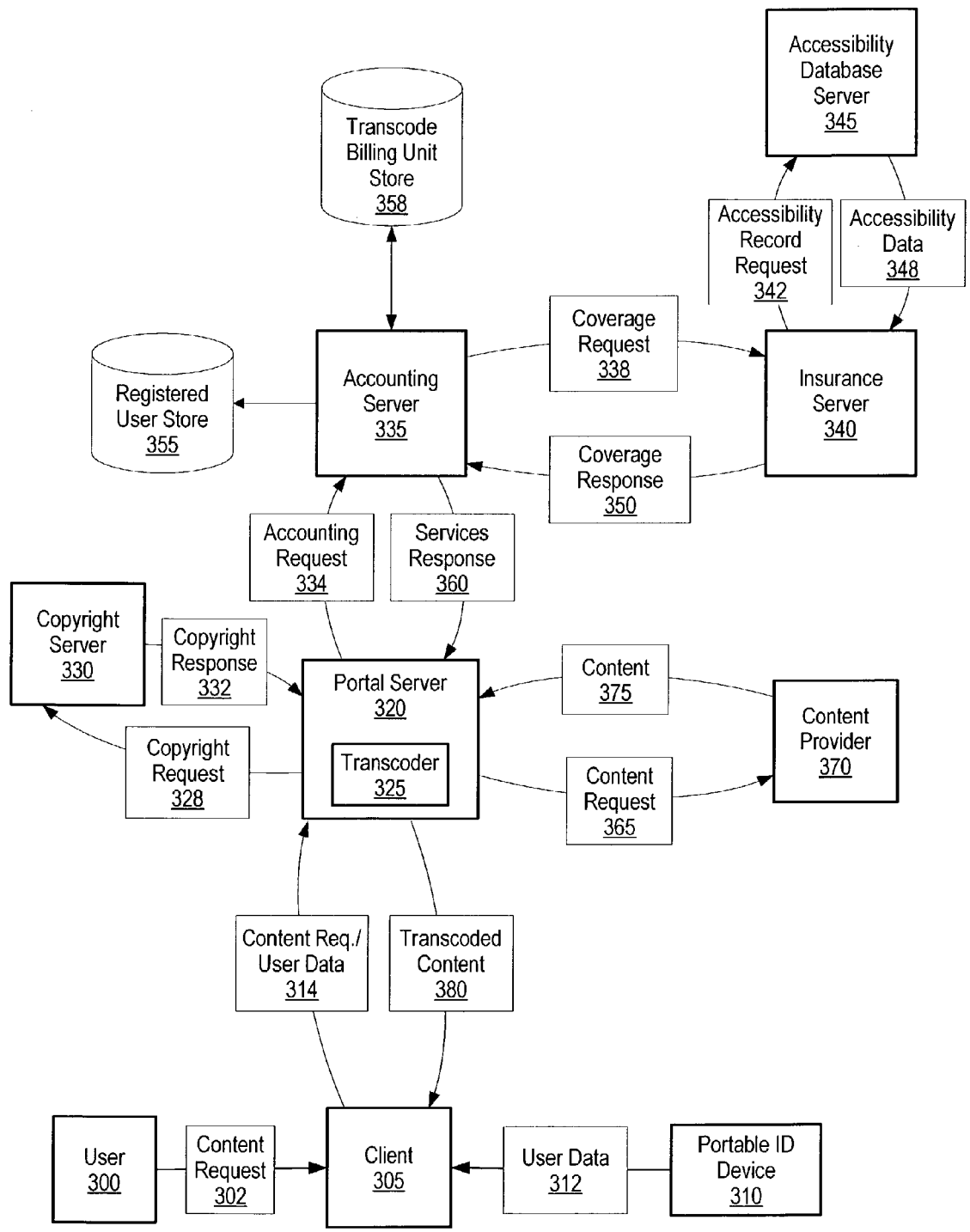
FIG. 3 is a diagram showing a portal server receiving a content request and processing the content request.

FIG. 3 is a diagram showing a portal server, such as portal server 320, receiving a content request and processing the content request. User 300 uses his pervasive computing device, such as pervasive computing device 310, to load user data 312 into client 305. User data 312 includes information corresponding to user 300, such as his user identifier, content presentation preferences, and billing information (see FIG. 8B and corresponding text for further details regarding user data). For example, user 300 may be blind and his user data informs a transcoder to transcode content request into "speech".

User 300 sends content request 302 to client 305. Content request 302 may be a request to access and to transcode content, such as a web page. Client 305 combines content request 302 and user data 312, and sends content request/user data 314 to portal server 320.

Portal server 320 extracts the content request from content request/user data 314, and sends content request 365 to content provider 370. Content request 365 corresponds to the content in which user 300 wishes to access. Content provider 370 receives content request 365, and sends content 375 to portal server 320. Using the example described above, content provider sends user 300's requested web page to portal server 320. Portal server 320 determines whether content 375 has copyright protection in regards to transcoding. For example, the content may be a page from a book novel and the content owner may not permit the content to be altered, or transcoded, without a fee.

When portal server 320 identifies that content 375 has copyright protection, portal server sends copyright request 328 to copyright server 330. Copyright server 330 analyzes the request, and may contact the content owner in order to determine stipulations and fees associated with transcoding the content (see FIG. 16 and corresponding text regarding copyright permissions). Copyright server 330 sends copyright response 332 to portal server 320 which includes a transcoding fee structure, if any, corresponding to transcoding content 375.

When a fee is associated with transcoding content, portal server 320 sends accounting request 334 to accounting server 330. Accounting server 335 tracks content transcoding events and manages account billings corresponding to the content transcoding events. Accounting request 334 includes user 300's user identifier. Accounting server 335 looks-up user 300's user identifier in registered user store 355 to determine if user 300 is registered. Registered user store 355 may be stored on a non-volatile storage area, such as a computer hard drive. If user 300 is registered and accounting server 335 has user 300's current billing information, accounting server sends services response 360 to portal server 320 which informs portal server 320 to transcode the requested content using transcoder 325. Portal server 320 transcodes the content, and sends transcoded content 380 to client 305. Accounting server 335 stores a transcoding fee, if any, along with user 300's user identifier in transcode billing store 358.

At frequent intervals, such as monthly, accounting server 335 performs a billing cycle. Accounting server 335 retrieves content transcoding information from transcode billing store 358, and sends coverage request 338 to insurance server 340 to identify whether user 300's insurance server covers content transcoding costs. Insurance server 340 receives coverage request 338 and identifies whether insurance server 340 has current accessibility data corresponding to user 300.

Insurance server 340 sends accessibility record request 342 to accessibility database server 345 to request current accessibility data corresponding to user 300. Accessibility record request 342 includes identifiers for both user 300 and insurance server 340. Accessibility database server 345 analyzes the request, and sends accessibility data 348 to insurance server 340 which includes accessibility data corresponding to user 300 based upon insurance server 340's access permissions (see FIG. 9A and corresponding text for further details regarding access permissions). Insurance server 340 analyzes user 300's current accessibility data, and sends coverage response 350 to accounting server 335 which includes an amount of user 300's content transcoding bill that insurance server 340 pays (i.e. 80%). Accounting server 335 receives the coverage information, and bills insurance server 340 and user 300 accordingly (see FIG. 15 and corresponding text for further details regarding account billing). In one embodiment, accounting server 335 sends payments to a content provider or content owner to obtain access permissions to transcode content.

FIG. 4 is a diagram showing a user using his pervasive computing device, such as pervasive computing device 405, to access a service. User 400 uses pervasive computing device 405 to request a service that service provider 420 provides. For example, service provider 420 may be a handicap parking garage and user 400 wishes to enter the parking garage. In this example, pervasive computing device 405 may be the user's mobile phone and the mobile phone communicates with an electronic parking attendant through a wireless network.

Pervasive computing device 405 sends access request 410 to service provider 420. Access request 410 includes user 400's user data such as his user identifier, insurance provider information, and accessibility privileges. Service provider 420 receives access request 410, and looks-up the user's user identifier in authorized user store 420. Service provider 420 uses authorized user store 420 to store authorized user's user identifiers. Authorized user store 425 may be stored on a non-volatile storage area, such as a computer hard drive.

If service provider 420 does not match user 400's user identifier in authorized user store 425, service provider 420 sends accessibility record request 450 to accessibility database provider 460 which includes a request for accessibility data corresponding to user 400. Accessibility record request 450 includes service provider 420's service provider identifier as well as user 400's user identifier. Accessibility database server 460 analyzes accessibility record request 450, retrieves accessibility data from accessibility database store 462, and sends accessibility data 465 to service provider 420. Accessibility data 465 includes user 400's accessibility data in which service provider 420 is permitted access (see FIGS. 9A, 19, 22A, and corresponding text for further details regarding accessibility data access permission).

Service provider 420 receives accessibility data 465 and determines that user 400 is authorized to receive the requested service. Using the example described above, service provider 420 determines that user 400 is entitled to enter the handicap parking garage. When a fee is charged for a service, service provider 420 sends coverage request 430 to insurance server 435 to check if insurance server 435 pays for user 400's requested service (i.e. parking garage fee). Insurance provider 435 analyzes coverage request 430, and sends coverage response 440 to service provider 420 which includes a payment amount that insurance provider 430 provides corresponding to user 400's service request (see FIG. 18 and corresponding text for further details regarding insurance provider coverage analysis).

Service provider 420 receives coverage response 440. If insurance provider 435 covers 100% of the service charge (i.e. parking garage fee), service provider authorizes user 400 for the particular service. On the other hand, if insurance provider 435 does not cover 100% of the service fee, service provider 420 sends charge authorization 470 to pervasive computing device 405. Using the example described above, the user's insurance provider may cover 50% of the parking garage fee, and the user is required to pay for the remaining 50% of the parking garage fee.

Pervasive computing device 405 sends payment 480 to service provider 420 to complete the service charge transaction. Payment 480 includes billing information corresponding to user 400, such as user 400's credit card information. In one embodiment, the service provider authorizes a user for a particular service, but does not charge the user. Using the example described above, the user may be entitled to free handicap parking, in which case the service provider validates handicap parking permission for the user without charging the user or the user's insurance server.

Figure 5:
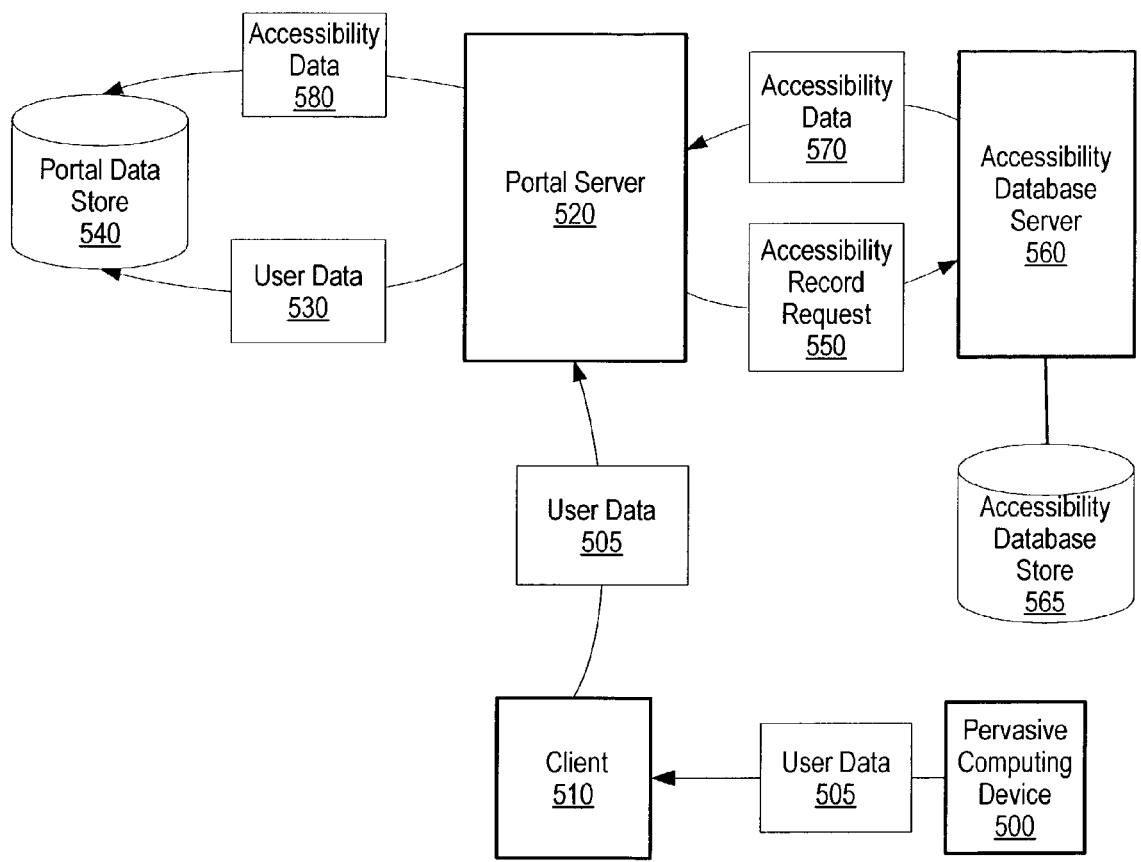
FIG. 5 is a diagram showing a portal server storing user information on a local storage area.

FIG. 5 is a diagram showing a portal server, such as portal server 520, storing user information on a local storage area. Portal server 520 is a server that manages user content transcoding requests. For example, portal server 520 may be Yahoo. A user uses his pervasive computing device, such as pervasive computing device 500, to load user data 505 into a client, such as client 510. User data 505 includes information, such as a user identifier, content presentation preferences, and billing information (see FIG. 8B and corresponding text for further details regarding user data properties).

Client 510 sends user data 505 to portal server 520 through a computer network, such as the Internet. Portal server 520 receives user data 505, and stores user data 530 in portal data store 540. Portal data store 540 may be stored on a non-volatile storage area, such as a computer hard drive.

Portal server 520 may wish to retrieve the user's accessibility types. If so, portal server 520 sends accessibility record request 550 to accessibility database server 560. Accessibility record request 550 includes a portal server identifier corresponding to portal server 520 as well as the user's user identifier. Accessibility database server 560 analyzes accessibility record request 550, retrieves accessibility data from accessibility database store 565, and sends accessibility data 570 to portal server 520. Accessibility data 570 includes accessibility data in which portal server is permitted access, such as the user's accessibility types (see FIGS. 9A, 19, 22B, and corresponding text for further details regarding accessibility data access permission).

Portal server 520 receives accessibility data 570, and stores accessibility privileges 580 on portal data store 540. Portal server 520 may access the user information in portal data store 540 during the user's next content request.

Figure 6:
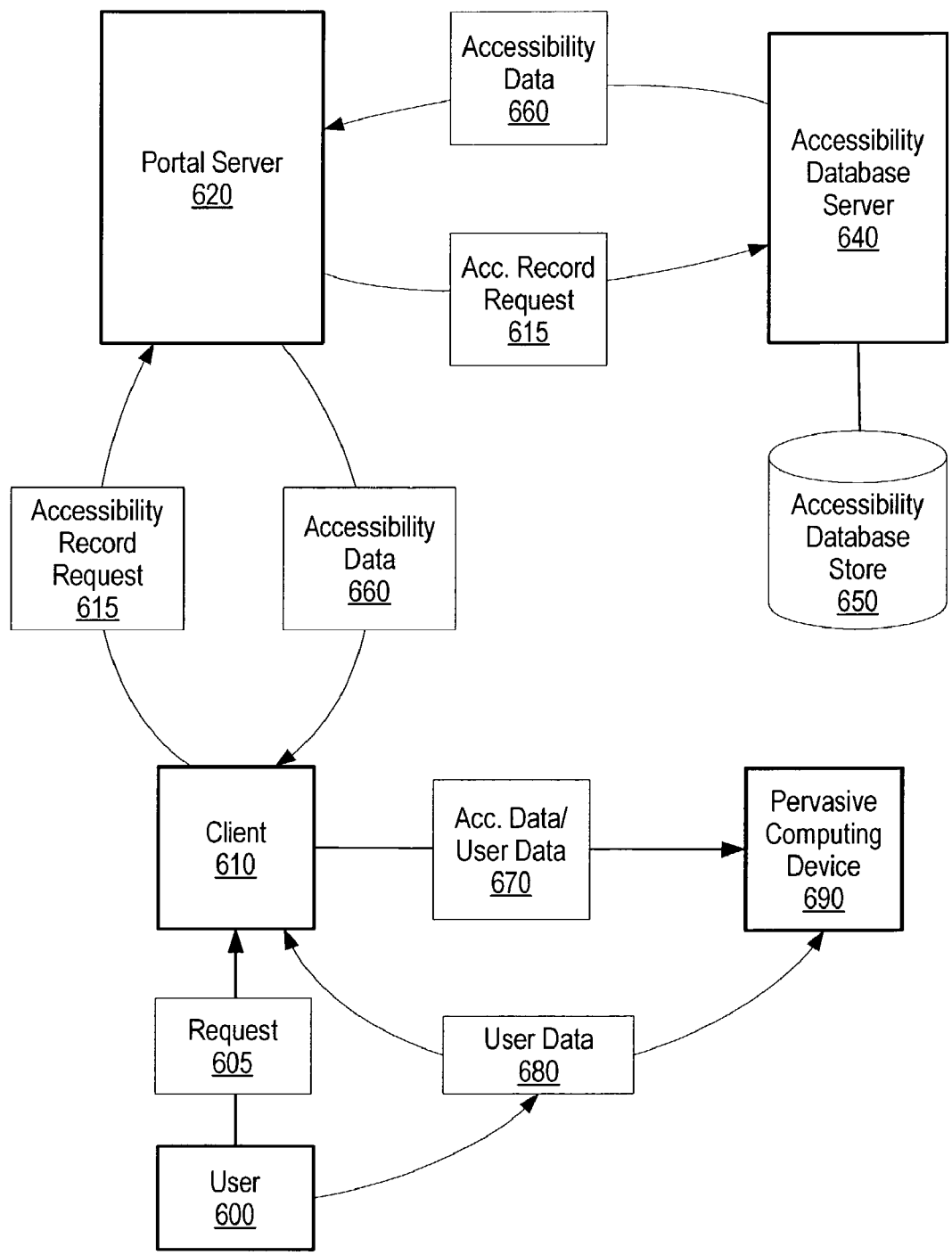
FIG. 6 is a diagram showing a user configuring a pervasive computing device.

FIG. 6 is a diagram showing a user configuring his pervasive computing device, such as pervasive computing device 690. User 600 wishes to load user data, such as the user's credit card number, and accessibility data, such as accessibility privileges, into pervasive computing device 690.

User 600 may load user data 680 directly into pervasive computing device 690 if pervasive computing device 690 includes a user interface, such as with a mobile phone or a personal digital assistant. In one embodiment, user 600 may use a client, such as client 610, to load user data into pervasive computing device 690 if pervasive computing device 690 does not include a user interface, such as with a smartcard.

User 600 sends request 605 to client 610 which includes a request to download user 600's accessibility data from accessibility database server 640. Request 605 includes user 600's user identifier. Client 610 sends accessibility record request 615 to portal server 620. Accessibility record request 615 includes user 600's user identifier. Portal server 620 forwards accessibility record request 615 to accessibility database server 640 for processing. Accessibility database server 640 analyzes the request, and retrieves accessibility data from accessibility database store 650. Accessibility database server 640 identifies user 600's user identifier to retrieve his accessibility data as well as identify which accessibility data user 600 is permitted access (see FIG. 9A and corresponding text for further details regarding database access permissions). Accessibility database store 650 may be stored on a non-volatile storage area, such as a computer hard drive.

Accessibility database server 640 sends accessibility data 660 to portal server 620. Portal server 620 forwards accessibility data 660 to client 610. Client 610 may combine user data with accessibility data and send accessibility data/user data 670 to pervasive computing device 690. User 600 may use pervasive computing device 690 to receive privileges, such as reduced bus fare, as well as use pervasive computing device 690 to load user information into a remote client in order to customize the content appearance on a remote client.

Figure 7:
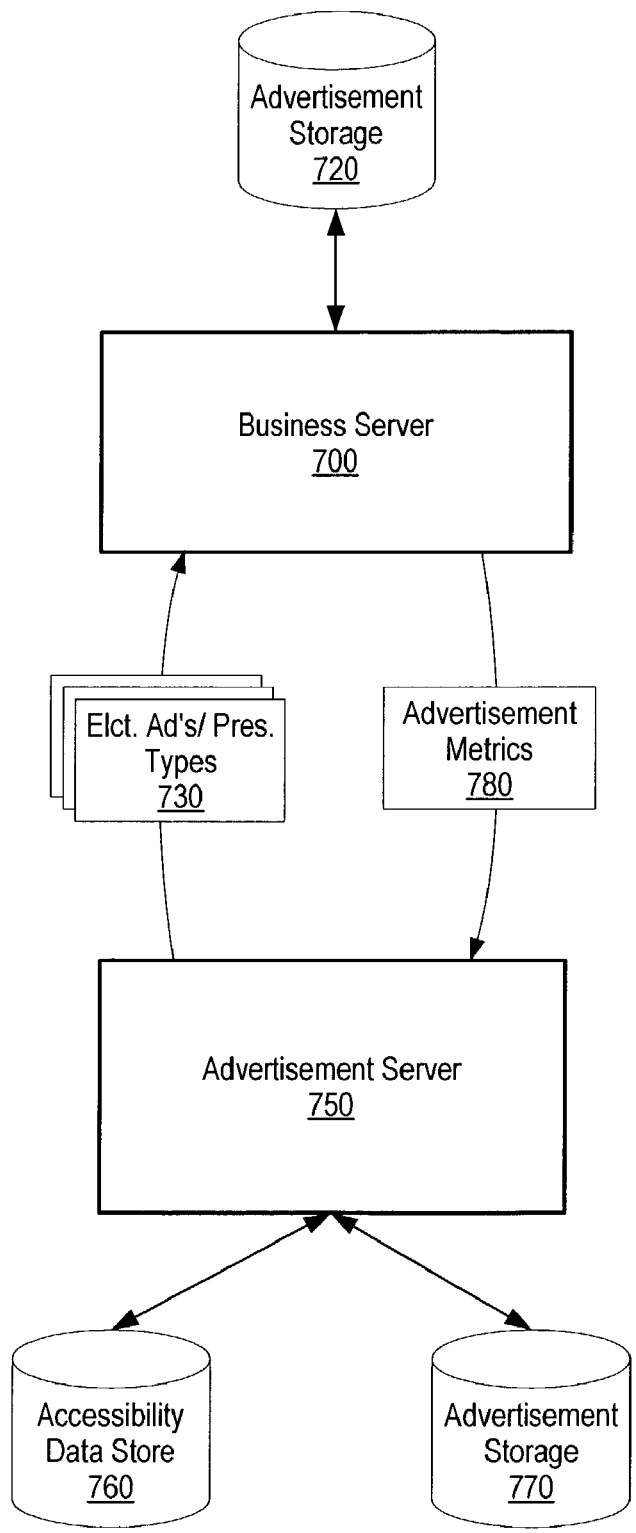
FIG. 7 is a diagram showing a business server sending electronic advertisements to an advertisement server.

FIG. 7 is a diagram showing a business sending electronic advertisements to an advertisement server, such as advertisement server 750. Advertisement server 750 provides electronic advertisements to individuals corresponding to the individual's preferences or accessibility type (see FIGS. 2, 17, and corresponding text for further details in regards to providing electronic advertisement). Advertisement server 750 receives advertisements from a business server, such as business server 700. For example, business server 700 may correspond to "The Soft Drink Company" and business server 700 wishes to use advertisement server 750 to send electronic advertisements to individuals.

Business server 700 transcodes particular advertisements using various transcoding settings. Business server 700 assigns a "presentation form" for each transcoded advertisement. For example, business server 700 may provide an advertisement in large font (i.e. "large font" presentation form) for a visually impaired person, as well as in speech (i.e. "speech" presentation form) for a blind person. Business server 700 stores the advertisements and corresponding presentation forms in advertisement store 720. Advertisement store 720 may be stored on a non-volatile storage area, such as a computer hard drive.

Business server 700 retrieves electronic advertisements and corresponding presentation form information from advertisement storage 720, and sends electronic advertisements/presentation forms 730 to advertisement server 750. Advertisement server 750 stores the presentation forms and the electronic advertisements in advertisement storage 770. Advertisement storage 770 may be stored on a non-volatile storage area, such as a computer hard drive.

As advertisement server 700 provides advertisements to users, advertisement server 750 tracks advertisement metrics and stores them in accessibility data store 760. The advertisement metrics may be used to inform business server 700 as to the amount of exposure his particular advertisements receive. For example, advertisement server 750 tracks the number of times each advertisement is sent to a user (see FIGS. 11A, 11B, and corresponding text for further details regarding advertisement metrics). On a periodic basis (i.e. monthly), advertisement server 750 retrieves advertisement metrics from accessibility data store 760, and sends advertisement metrics 780 to business server 700. Business server 700 may analyze the advertisement metrics to assess whether its contract with advertisement server 750 requires adjustment. For example, business server 700 may determine that it wishes to increase the amount of times his particular advertisements are sent to users and in doing so, business server 700 is willing to increase funding to advertisement server 750.

FIG. 8A shows a user interface window in which a user selects choices to configure user data. Processing displays configuration window 800 on a client's display when processing receives a request from the user to configure user data (see FIG. 25 and corresponding text for further details regarding configuration requests). User data may be stored on a client, a user's pervasive computing device, or a portal server.

Configuration window 800 includes text fields (i.e. text boxes) user identifier text field 805 and password text field 808. The user enters his user identifier in user identifier text field 805 and his corresponding password in password text field 808 in order to log in to configuration window 800. In one embodiment, configuration window may retrieve the user's user identifier and password from the user's personal identification device and display his user identifier and password in user identifier text field 805 and password text field 808, respectively.

Configuration window 800 includes three command buttons which are configure command button 810, format command button 815, and synchronize command button 820. The user selects configure command button 810 to configure user data such as changing the user's password, modifying content presentation preferences, and entering account billing information (see FIG. 8B and corresponding text for further details regarding user data configuration).

The user selects format command button 815 to format the user's personal identification device. For example, the user's personal identification device may be a smartcard and the user may wish to format the smartcard's memory (see FIG. 25 and corresponding text for further details regarding personal identification device formatting). The user selects synchronize command button 820 to synchronize his personal identification device with a client. For example, the user may wish to upload new content presentation preference information located on his personal identification device to his client (see FIGS. 25, 26, and corresponding text for further details regarding personal identification device synchronization).

FIG. 8B shows a user preferences interface window that a user uses to view and modify his user data. User data window 825 includes user preferences that correspond to how a user requests content to be presented. For example, a user may have a vision impairment and wish to magnify text in order to view the text more clearly. Another example is that a user may not prefer flashing advertisements and configures his user preferences so that presented content does not include flashing advertisements.

User data window 825 includes user log on information, content presentation preferences, and billing information. User identifier text field 830 and password text field 832 include the user's user identifier and the user's password that the user entered in a configuration window (see FIG. 8A and corresponding text for further details regarding configuration windows).

User data window 825 includes content presentation text fields for the user to customize how content is presented. For example the user may be visually impaired and wish to have font sizes increased, background pictures removed, and stop flashing advertisements from flashing. The user enters a font magnification amount in zoom text field 835 which informs a transcoding device to increase or decrease the font size of requested content. The user enters a "Yes" or "No" selection in sharpen image text field 840 which, if "Yes" is entered, informs a transcoding device to sharpen the image of a selected content to transcode (i.e. increase the contrast, increase the resolution, color substitution, etc.).

The user enters a "Yes" or "No" selection in stop animator text field 845 which, if "Yes" is entered, informs a transcoding device to stop objects from moving on requested content. The user enters a "Yes" or "No" selection in stop flashing text field 850 which, if "Yes" is entered, informs a transcodinq device to stop areas of the content from flashing, such as a flashing advertisements.

The user enters a "Yes" or "No" selection in left justify text field 855 which, if "Yes" is entered, informs a transcoding device to left justify text and pictures. Left justify may be useful when a user increases the font size to a level in which an entire line does not fit on a display. The user enters a "Yes" or "No" selection in mouseover text field 860 which, if "Yes" is entered, informs processing to shift, or move, the displayed screen corresponding to mouse movements. For example, the user moves his mouse to the right side of the display and processing shifts the display corresponding to the mouse location. Mouseover may be useful when a user increases the font size to a level in which an entire line does not fit on a display. The user enters a "Yes" or "No" selection in remove background text field 865 which, when "Yes" is entered, informs a transcoding device to remove the background of selected content. In one embodiment, user data window 825 may include other presentation text fields, such as a speech selector field, a high contrast field, a text spacing field, and a line field.

User data window 825 also includes billing information corresponding to the user, such as credit card information and insurance provider information. Processing provides billing information to portal servers and service providers when the user requests a particular service, such as content transcoding or accessing a handicap parking garage. The user enters his credit card type, such as "Visa" in card type text field 870. The user enters his credit card number in card number text field 875. The user enters his credit card's expiration date in card expiration text field 880.

If the user is insured, the user enters the name of his insurance provider in insurance name text field 885. The user also enters the insurance provider's corresponding insurance identifier in insurance identifier text field 890.

FIG. 9A shows an accessibility permission look-up table, such as look-up table 900, that identifies access permissions for various requestors. An accessibility database provider uses look-up table 900 to identify access permissions based upon a particular requestor (see FIG. 19 and corresponding text for further details regarding requestor identification).

Look-up table 900 includes a list of requestor types that request access to an accessibility database. Row 905 includes access permissions when a user requests access. Row 910 includes access permissions when a health care practitioner requests access. Row 915 includes access request permissions when an insurance server requests access. Row 920 includes access request permissions when a service provider requests access. Row 925 includes access permissions for when an advertisement server requests access or when a portal server requests access.

Column 930 includes requestor access permissions to enter accessibility type information (i.e. broken leg). The example shown in FIG. 9A illustrates that a health care practitioner is allowed to enter accessibility type information. The healthcare practitioner, however should have access permission to a user accessibility record (see FIG. 9B and corresponding text for further details regarding healthcare practitioner access permission). Column 935 includes requestor access permissions to enter healthcare practitioner identifiers. The example shown in FIG. 9A illustrates that a user is allowed to enter healthcare practitioner identifiers. Column 940 includes requestor access permissions to enter accessibility privileges. The example shown in FIG. 9A illustrates that a health care practitioner is allowed to enter accessibility privileges (i.e. reduced bus fare). The healthcare practitioner however should have access permission to a user accessibility record (see FIG. 9B and corresponding text for further details regarding healthcare practitioner access permission).

Column 945 includes requestor access permissions to retrieve accessibility type information corresponding to a user identifier. The example shown in FIG. 9A illustrates that a user and a healthcare practitioner are allowed to retrieve accessibility types corresponding to the user's accessibility record (i.e. broken leg). Column 950 includes requestor access permissions to retrieve healthcare practitioner identifiers corresponding to a user identifier. The example shown in FIG. 9A illustrates that a user and a healthcare practitioner are allowed to retrieve healthcare practitioner identifiers. Column 955 includes requestor access permissions to retrieve accessibility privilege information corresponding to a user identifier. The example shown in FIG. 9A illustrates that a user, a healthcare practitioner, an insurance server, a service provider, an advertisement server, and a portal server are allowed to retrieve accessibility privilege information corresponding to a user identifier (i.e. reduced bus fare).

FIG. 9B shows a user accessibility record window, such as user accessibility window 960, which includes accessibility data corresponding to a user identifier. Row 965 shows accessibility data information corresponding to user identifier "U12345".

Column 970 shows accessibility types corresponding to the user identifier. The example shown in FIG. 9B illustrates that user identifier "U12345" has "impaired vision" and "broken leg" accessibility types. Column 975 shows healthcare practitioner identifiers corresponding to healthcare practitioners that are treating the user's accessibility types. The example shown in FIG. 9B illustrates that healthcare practitioner identifier "P98765" is treating the user's impaired vision. The accessibility database provider uses healthcare practitioner identifiers to determine access permissions (see FIG. 9A and corresponding text for further details regarding access permissions).

Column 980 shows accessibility privileges corresponding to the user's accessibility types. The example shown in FIG. 9B illustrates that the user has a "handicap parking" accessibility privilege corresponding to his "impaired vision" accessibility type. Column 985 shows privilege expiration dates corresponding to accessibility privileges. The example shown in FIG. 9B illustrates that the user's "reduced bus fair" accessibility privilege expires in May 2002.

FIG. 10 shows an insurance server's policy holder look-up table, such as look-up table 1000, which includes information corresponding to policy holders. The insurance server uses look-up table 1000 to verify that a user is a policy holder. The insurance server also uses look-up table 1000 to authorize insurance coverage corresponding to a user accessibility type. The insurance server receives coverage requests from accounting servers and service providers. The coverage requests include a user identifier and an accessibility validation request. The insurance server uses the user identifier to verify the corresponding user is a policy holder. The insurance company then uses the accessibility validation request to authorize insurance coverage corresponding to a particular event. For example, a user may request a web page to be transcoded and the insurance server authorizes payments if the user is insured for a "content transcoding" accessibility privilege.

Look-up table 1000 includes five columns which are column 1030, column 1040, column 1050, column 1060, and column 1070. Column 1030 includes user identifiers corresponding to policy holders. The example in FIG. 10 shows that users corresponding to user identifier U12345 and user identifier U45678 are policy holders with the particular insurance provider.

Column 1040 includes accessibility types corresponding to user identifiers. Accessibility types indicate a user's particular accessibility issue, or impairment. The example in FIG. 10 shows that the user corresponding to user identifier "U12345" has a "broken leg" accessibility type.

Column 1050 includes accessibility privileges corresponding to user identifiers. Accessibility privileges identify services that the corresponding user has insurance coverage. The example in FIG. 10 shows that the user corresponding to user identifier "U12345" is authorized free bus fare and free wheelchair use.

Column 1060 includes an amount of claims paid to date corresponding to a particular accessibility privileges. The insurance company may use this information to track when a user reaches a maximum coverage level. For example, the user may have a policy that allows up to $200 for after-accident expenses, such as wheelchairs and bus fare. In this example, the insurance provider authorizes after-accident expenses until the user reaches his limit, at which point the insurance provider denies further after-accident expenses and the user pays for the expenses incurred after the limit is reached.

Column 1070 includes database update information corresponding to user identifiers. The insurance company uses this information to ensure that policy holder look-up table 1000 includes up-to-date information. The insurance provider frequently accesses an accessibility database to download relevant accessibility data corresponding to a particular user identifier (see FIGS. 3, 18, and corresponding text for further details regarding insurance database updates).

FIG. 11A shows an advertisement tracker look-up table, such as look-up table 1100, in which an advertisement server uses to track advertisement metrics. An advertisement server uses look-up table 1100 to track the amount of times that an advertisement is provided to a user. Look-up table 1100 includes five columns which are presentation form column 1110, advertisement identifier column 1120, advertisement weighting column 1130, times provided column 1140, and hit rate column 1150.

Presentation form column 1110 includes presentation forms corresponding to transcoded advertisements. Presentation forms correspond to user accessibility types are used to categorize advertisements. The example in FIG. 11A shows two presentation forms which are "Blind" and "Seizures". In this example, advertisements corresponding to a "Blind" impairment type may be "spoken" advertisements. In one embodiment, the advertisement server may have varying degrees of contrast accessibility types to categorize advertisements in a manner suitable to varying degrees of visual impairments.

Advertisement identifier column 1120 includes advertisement identifiers corresponding to advertisements. The advertisement server uses advertisement identifiers to track advertisement metrics for each advertisement, such as the number of times an advertisement is provided to a user. Advertisement weighting column 1130 includes a weighting factor for each advertisement. The advertisement tracker uses advertisement weightings during the process of identifying which advertisement to provide to a user. For example, if an advertisement has a high weighting, such as "5", the advertisement tracker may provide the particular advertisement five times more frequently than an advertisement that has a weighting of "1". The advertisement tracker may also charge a customer different prices based upon which advertisement weighting the customer chooses for his particular advertisement.

Times provided column 1140 includes a number of times a particular advertisement has been provided to a user. The advertisement tracker increments this number for a particular advertisement each time the advertisement is sent to a portal for inclusion in a response to the user (see FIGS. 2, 13, 17, and corresponding text for further details regarding advertisement inclusion). Hit rate column 1150 includes a percentage of times that a user selected the advertisement for further information. For example, a car rental advertisement may provide a user with promotional fares when the user selects the advertisement.

FIG. 11B shows a user advertisement tracker look-up table, such as look-up table 1160, that an advertisement server uses to track user metrics. Look-up table 1160 includes four columns which are user identifier column 1170, accessibility type column 1180, last advertisement identifier column 1190, and number of advertisements column 1195.

Figure 13:
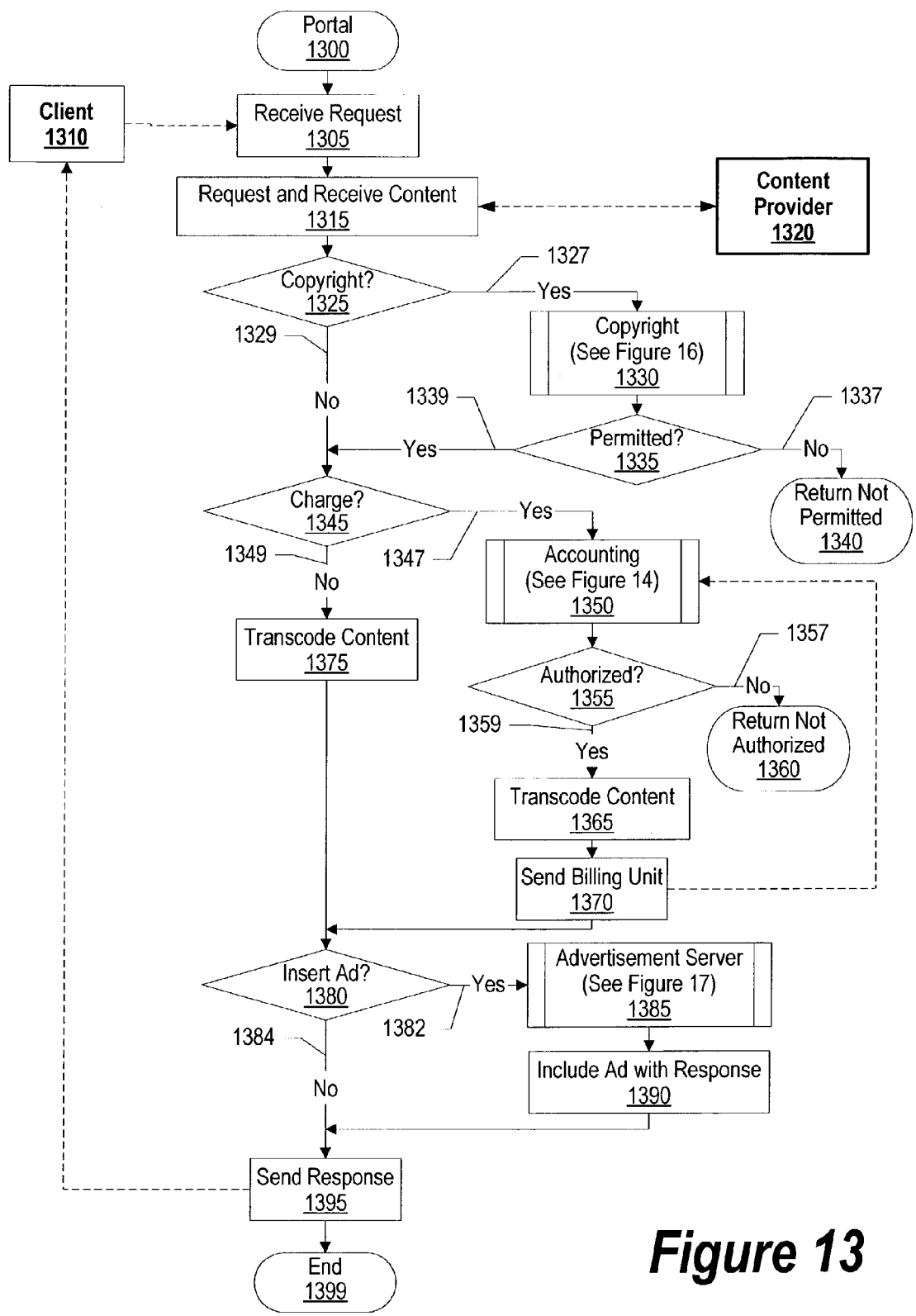
FIG. 13 is a flowchart showing steps taken in a portal server receiving a client request and processing the client request.

User identifier column 1170 includes a list of user identifiers corresponding to users that have requested content from a portal server and the advertisement provider has provided an advertisement to the user (see FIGS. 2, 13, 17, and corresponding text for further details in regards to providing advertisements). Accessibility type column 1180 includes accessibility types corresponding to each user identifier. The example in FIG. 11B shows that user identifier "U12345" corresponds to a "blind" accessibility type.

Last advertisement identifier column 1190 includes an advertisement identifier of the last advertisement that was provided to a corresponding user identifier. The advertisement tracker uses the advertisement identifiers in this column to identify the next advertisement to provide when a particular user requests content. Number of advertisements column 1195 includes a number of times that the advertisement server provided an advertisement to a particular user identifier. The advertisement server may use information in this column to identify which users are frequent content requestors.

In one embodiment, due to privacy concerns, the advertisement server does not store user information in a lookup table but rather receives pertinent user information during a request from a requestor.

FIG. 12 shows an accounting service look-up table, such as accounting service look-up table 1200, which an accounting service uses to identify user payment options. The accounting server receives accounting requests from a portal in which the accounting request corresponds to a user's content transcoding request. For example, the user may be blind and the user is requesting the portal to transcode a particular web page into a "spoken web page" (see FIGS. 3, 13, 14, 15, and corresponding text for further details regarding accounting requests).

Accounting look-up table 1200 includes six columns which are column 1210, column 1220, column 1230, column 1240, column 1250, and column 1260. Column 1210 includes user identifiers corresponding to users that are registered with the accounting server. Column 1220 includes accessibility types corresponding to user identifiers. The example in FIG. 12 shows that the user corresponding to user identifier U12345 has a "blind" accessibility type.

Column 1230 includes content transcoding insurance coverage information corresponding to user identifiers. The accounting server stores insurance coverage information in look-up table 1200 so the accounting service does not have to request information from an insurance server each time one of the insurance server's policy holders requests content transcoding.

Column 1240 includes insurance server identifiers that correspond to the user identifiers. The accounting service uses the insurance server identifiers to identify a particular user's insurance company. In one embodiment, the user provides his insurance server's insurance server identifier when the user registers with the accounting service.

Columns 1250 and 1260 include a user's personal billing information corresponding to a particular user identifier. Column 1250 includes user billing information, such as the user's credit card number, that the accounting server may use if the user's insurance server does not cover the entire cost of a content transcoding event. Column 1260 includes other user information, such as a user's address, in which the accounting uses for various activities, such as mailing a billing statement.

FIG. 13 is a flowchart showing steps taken in a portal server receiving a client request and processing the client request. Portal server processing commences at 1300, whereupon a request is received from client 1310 at step 1305. The request includes a request to provide content based upon the user's needs, such as the content of a web page. Processing requests and retrieves the requested content from content provider 1320 at step 1315.

A determination is made as to whether the requested content is copyright protected (decision 1325). If the requested content is not copyright protected, decision 1325 branches to "No" branch 1329 bypassing copyright permission steps. On the other hand, if the requested content is copyright protected, decision 1325 branches to "Yes" branch 1327 whereupon processing checks if the requested content's owner permits content transcoding (pre-defined process block 1330, see FIG. 16 and corresponding text for further details regarding permission checking).

A determination is made as to whether the content owner permits content transcoding for the requested content (decision 1335). For example, the content owner may charge a "transcode fee" for transcoding his content. If the copyright owner does not permit transcoding for the requested content, decision 1335 branches to "No" branch 1337 whereupon not permitted is returned to client 1310 at 1340. On the other hand, if the content owner permits transcoding of the requested content, decision 1335 branches to "Yes" branch 1339.

A determination is made as to whether a transcode fee exists to transcode the requested content (decision 1345). If there is not a transcode fee to transcode the requested content, decision 1345 branches to "No" branch 1349 whereupon processing transcodes the requested content at 1375. In one embodiment, the portal server may request a transcoding proxy server to perform content transcoding functions. On the other hand, if a transcoding fee exists to transcode the requested content, decision 1345 branches to "Yes" branch 1347 whereupon accounting services identifies whether payment is authorized for a content transcoding event (pre-defined process block 1350, see FIG. 14 and corresponding text for further details regarding payment authorization).

A determination is made as to whether payment is authorized to transcode the requested content (decision 1355). If payment is not authorized, decision 1355 branches to "No" branch 1357 whereupon not authorized is returned to client 1310 at 1360. On the other hand, if payment is authorized, decision 1355 branches to "Yes" branch 1359 whereupon processing transcodes the requested content at step 1365. Processing sends a transcoding fee corresponding to the transcode process to accounting server at step 1370. The transcoding fee identifies the requested content and the user that requested the transcoding process. The accounting server uses the transcoding fee during a billing cycle to calculate a customer's (see FIG. 15 and corresponding text for further details regarding billing cycles).

A determination is made as to whether to insert an electronic advertisement with the transcoded content (decision 1380). If processing should not insert an electronic advertisement, decision 1380 branches to "No" branch 1384, bypassing advertisement insertion steps. On the other hand, if processing should insert and advertisement, decision 1380 branches to "Yes" branch 1382 whereupon a request is sent to an advertisement server requesting an advertisement (pre-defined process block 1385, see FIG. 17 and corresponding text for further details regarding advertisement processing). Processing receives an electronic advertisement from the advertisement provider, and includes the electronic advertisement with the transcoded content at step 1390.

Processing sends a response to client 1310 that includes the transcoded content and may include an electronic advertisement (step 1395). Processing ends at 1399.

Figure 14:
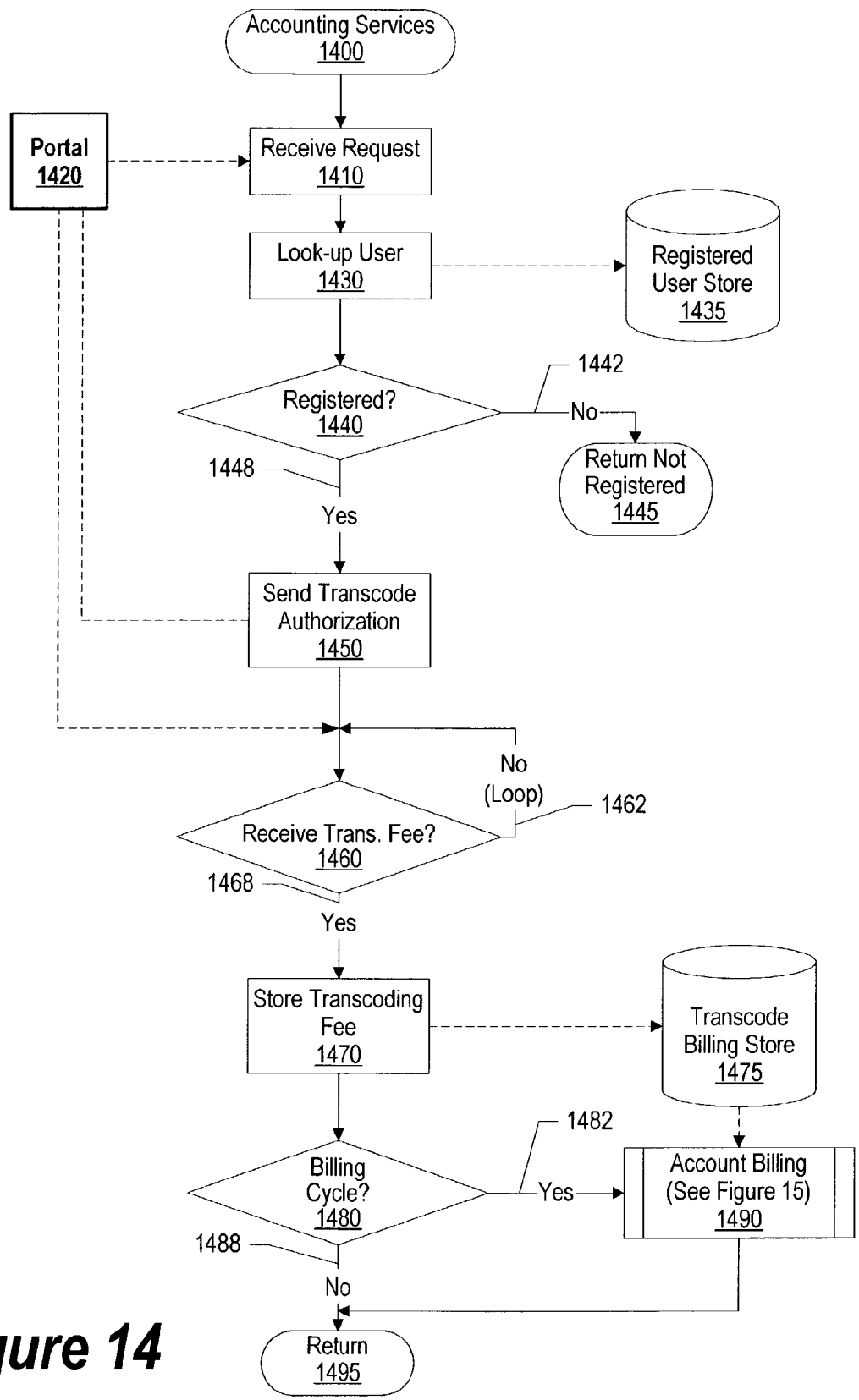
FIG. 14 is a flowchart showing steps taken in an accounting server receiving an accounting request from a portal server and processing the accounting request.

FIG. 14 is a flowchart showing steps taken in an accounting server receiving an accounting request from a portal server and processing the accounting request. The accounting request corresponds to the portal transcoding content that is billable wherein the accounting server manages the accounting aspects of billing customers.

Processing commences at 1400, whereupon the accounting server receives a request from portal 1420 at step 1410. The request includes a user identifier corresponding to a user requesting to transcode content. For example, the user may request to transcode a web page that has copyright permissions, but the content transcoding event requires a payment. Processing looks-up the user identifier in registered user store 1435. Processing stores a list of registered users in user storage 1435 wherein the list includes user identifiers, and may include personal information, such as the user's name, email address, and telephone number (see FIG. 12 and corresponding text for further details regarding registered user entry properties).

A determination is made as to whether the user is registered (decision 1440). If the user is not registered, decision branches to "No" branch 1442 whereupon "Not Registered" is returned at 1445. If the user is not registered, the user may be required to log on to the accounting server website and register with the server. In one embodiment, the user may register with the accounting server using a portal server, such as Yahoo.

On the other hand, if the user is registered, decision 1440 branches to "Yes" branch 1448 whereupon processing sends an authorization to transcode the requested content to portal 1420 (step 1450). A determination is made as to whether processing received a transcoding fee from portal 1420 (decision 1460). If portal 1420 is not finished transcoding the content, decision 1460 branches to "No" branch 1462 which loops back to continue to check if portal 1420 is finished transcoding the content. This looping continues until portal 1420 sends a transcoding fee, at which point decision 1460 branches to "Yes" branch 1468.

Processing stores a transcoding fee in transcode billing store 1475 (step 1470). The transcoding fee includes the user identifier corresponding to the user that requested the transcoding process. The transcoding fee also includes a content identifier that identifies the transcoded content. The content identifier is used to identify who is paid as a result of the transcoding process. Using the example described above, the website owner may be paid a fee as a result of portal 1420 transcoding the copyrighted content.

A determination is made as to whether it is time for processing to perform a billing cycle (decision 1480). Billing cycles may occur on a frequent basis, such as monthly. If it is time for a billing cycle, decision 1480 branches to "Yes" branch 1482 whereupon accounts are billed by using transcode fee information located in transcode billing store 1475 (pre-defined process block 1490, see FIG. 15 and corresponding text for further details). On the other hand, if it is not time for a billing cycle, decision 1480 branches to "No" branch 1488 bypassing account billing steps. Processing returns at 1495.

Figure 15:
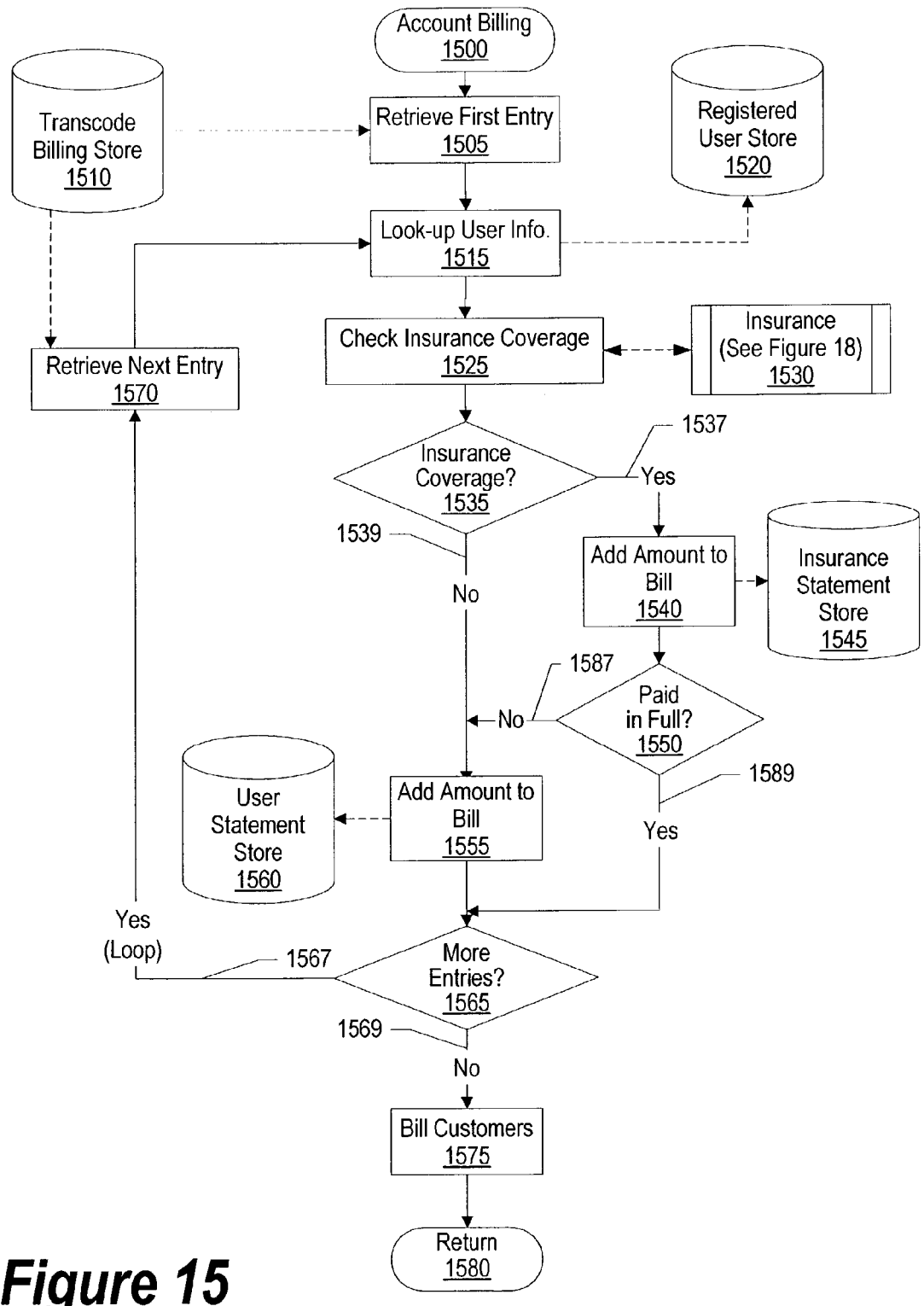
FIG. 15 is a flowchart showing steps taken in an accounting server billing accounts corresponding to previously transcoded content events.

FIG. 15 is a flowchart showing steps taken in an accounting server billing accounts corresponding to previously transcoded content events. Processing commences at 1500, whereupon processing retrieves a first transcode fee from transcode billing store 1510. The transcode fee includes a user identifier corresponding to a user that requested content to be transcoded, as well as a content identifier that informs processing who is paid for the transcoding event (see FIGS. 13, 14, and corresponding text for further details regarding content transcoding requests). Transcode billing store 1510 may be stored on a non-volatile storage area, such as a computer hard drive.

Processing looks-up the user identifier in a user look-up table located in registered user store 1520. For example, the user look-up table includes a user identifier, an impairment type, insurance coverage information, an insurance identifier, and personal information See FIG. 12 and corresponding text for further details regarding look-up table properties). Registered user store 1520 may be stored on a nonvolatile storage area, such as a computer hard drive. Processing uses the insurance identifier to check insurance coverage of the user for content transcoding events or accessibility services (step 1525). The insurance company receives the request, analyzes the request, and returns coverage information (pre-defined process block 1530, see FIG. 18 and corresponding text for further details regarding insurance processing).

A determination is made as to whether the user's insurance pays for a portion of content transcoding events (decision 1535). If processing determined that the user's insurance coverage does not cover content transcoding events, decision 1535 branches to "No" branch 1539 bypassing insurance coverage steps. On the other hand, if the user's insurance pays for a portion of the service, decision 1535 branches to "Yes" branch 1537 whereupon processing bills the user's insurance company account located in insurance statement store 1545 (step 1540). Insurance statement store 1545 may be stored on a non-volatile storage area, such as a computer hard drive.

A determination is made as to whether the user's insurance coverage covers 100% of content transcoding events (decision 1550). For example, the user's insurance server may pay only 50% of the cost of content transcoding events. If the user's insurance coverage pays 100% of content transcoding events, decision 1550 branches to "Yes" branch 1589, bypassing user billing steps.

On the other hand, if the insurance server does not pay 100% of content transcoding fees, decision 1550 branches to "No" branch 1587. Processing bills the user's account located in user statement store 1560 for the remaining charge of the content transcoding fee (step 1555). User statement store 1560 may be stored on a non-volatile storage area, such as a computer hard drive.

A determination is made as to whether there are more transcode fee entries in transcode billing store 1510 (decision 1565). If there are more transcode fee entries, decision 1565 branches to "Yes" branch 1567 which loops back to retrieve (step 1570) and process the next transcode fee. This looping continues until there are no more transcode fees to process, at which point decision 1565 branches to "No" branch 1569.

Processing sends user and insurance bills at step 1575. In one embodiment, processing receives electronic payments from customers (i.e. the user and the insurance server) and tracks payment history. In another embodiment, processing automatically debits user and insurance company accounts for faster payments. Processing returns at 1580.

Figure 16:
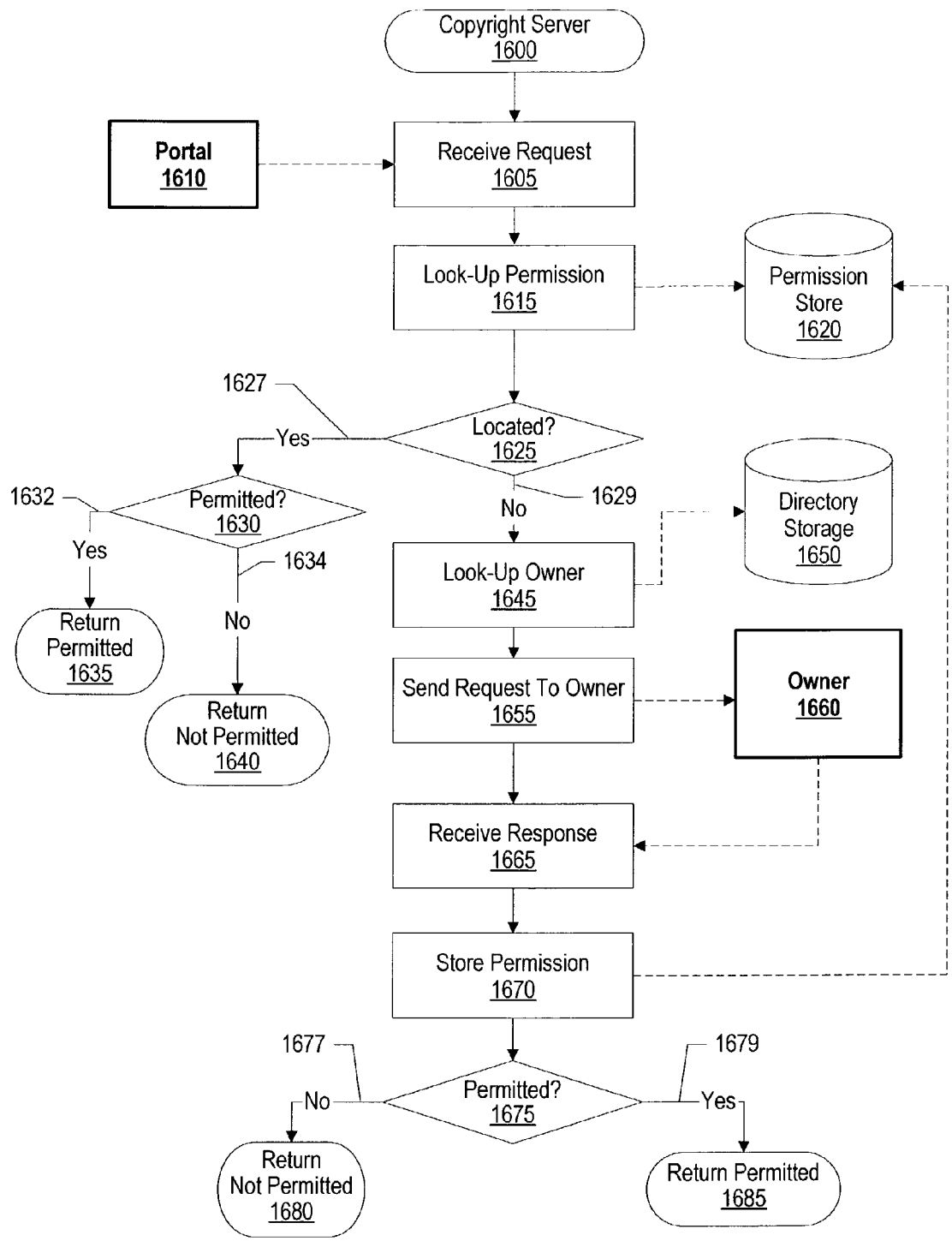
FIG. 16 is a flowchart showing a copyright server receiving a request and identifying whether corresponding content is permissible to transcode.

FIG. 16 is a flowchart showing a copyright server receiving a request and identifying whether corresponding content is permissible to transcode. Copyright server processing commences at 1600, whereupon processing receives a request from portal 1610 at step 1605. The request corresponds to content that portal 1610 wishes to transcode. For example, portal 1610 may have received a request from a user that has a vision impairment.

Processing looks-up permission rights corresponding to the requested contents in permission store 1620 (step 1615). Permission store 1620 may be stored on a nonvolatile storage area, such as a computer hard drive. A determination is made as to whether processing located permission rights corresponding to the requested content (decision 1625). If processing located permission rights corresponding to the requested content, decision 1625 branches to "Yes" branch 1627 whereupon a determination is made as to whether the requested content is permitted to be transcoded (decision 1630). If the requested content is permitted to be transcoded, decision 1630 branches to "Yes" branch 1632 whereupon "Permitted" is returned at 1635. On the other hand, if the requested content is not permitted to be transcoded, decision 1630 branches to "no" branch 1634 whereupon "Not Permitted" is returned at 1640.

If processing did not locate the requested content's permission rights in permission store 1620, decision 1625 branches to "No" branch 1629 whereupon the owner of the requested content is looked-up in directory storage 1650 (step 1648). For example, a requested web page owner is looked-up and the web page owner's email address is retrieved. Directory storage 1650 may be stored on nonvolatile storage area, such as a computer hard drive. In one embodiment, processing may access a global directory server over a computer network, such as the Internet.

Processing sends a permission request to owner 1660 wherein the permission request includes a request to transcode the requested content (step 1655). Owner 1660 may correspond to a copyright authorization server or owner 1660 may correspond to a copyright owner's or agent's email account. Owner 1660 receives the request, analyzes the request, and sends a response to the copyright server. Processing receives owner 1660's response at step 1665. The response includes whether the requested content is permissible to transcode. The permission rights corresponding to the requested content are stored in permission store 1620 at step 1670.

A determination is made as to whether the requested content is permissible based upon owner 1660's response (decision 1675). If owner 1660 does not permit the requested content to be transcoded, decision 1675 branches to "No" branch 1677 whereupon "Not Permitted" is returned at 1680. On the other hand, if owner 1610 permits the requested content to be transcoded, decision 1675 branches to "Yes" branch 1679 whereupon "Permitted" is returned at 1685.

FIG. 17 is a flowchart showing an advertisement server receiving a request from a portal server or web server, identifying an electronic advertisement, and sending the electronic advertisement to the portal. Processing commences at 1700, whereupon processing receives an advertisement request from portal 1710 at step 1705. The advertisement request includes a user identifier corresponding to a user that is requesting content. In one embodiment, the advertisement request includes a presentation form, such as "spoken advertisement", wherein processing uses the presentation form to identify a suitable advertisement.

Processing looks-up the user identifier in a look-up table located in user identifier store 1720 (step 1715). User identifier store 1720 may be stored on a nonvolatile storage area such as a computer hard drive. In one embodiment, due to privacy concerns, processing does not store user information on a non-volatile storage area but rather receives the user information in the request. A determination is made as to whether processing matched the user identifier with an entry in the lookup table (decision 1725). If processing matched the user identifier with the lookup table located in user identifier store 1720, decision 1725 branches to "Yes" branch 1729, bypassing accessibility type request and storage steps.

On the other hand, if processing did not match the user identifier with an entry in the look-up table, decision 1725 branches to "No" branch 1727 whereupon a determination is made as to whether one or more accessibility types corresponding to the user identifier were included in the advertisement request (decision 1730) (see FIG. 11B and corresponding text for further details regarding accessibility types).

If accessibility types were included with the advertisement request, decision 1730 branches to "Yes" branch 1734, bypassing accessibility data requesting steps. On the other hand, if one or more accessibility types were not included in the advertisement request, decision 1730 branches to "No" branch 1732 whereupon processing requests accessibility data from an accessibility database server at step 1735 (predefined process block 1740, see FIG. 19 and corresponding text for further details). Processing receives the accessibility database server's response at step 1745 which includes accessibility data corresponding to the user identifier, and stores the user identifier and corresponding accessibility types in user identifier store 1720 at step 1750. In one embodiment, due to privacy concerns, processing does not store user information on a non-volatile storage area but rather discards the information once processing identifies a user's presentation form preference.

Processing identifies an electronic advertisement suitable for the user, and retrieves the identified electronic advertisement from advertisement store 1760 at step 1755. Processing identifies which advertisement to select by using advertisement tracker look-up tables. The advertisement tracker also tracks which advertisement has been previously provided to the corresponding the user (see FIGS. 11A, 11B, and corresponding text for further details regarding advertisement look-up tables). Processing increments the advertisement tracker table located in advertisement store 1760 at step 1765.

Processing sends electronic advertisement 1775 to portal 1710 at step 1770. For example, electronic advertisement 1775 may be a "spoken" advertisement for a blind user. Processing returns at 1780.

Figure 18:
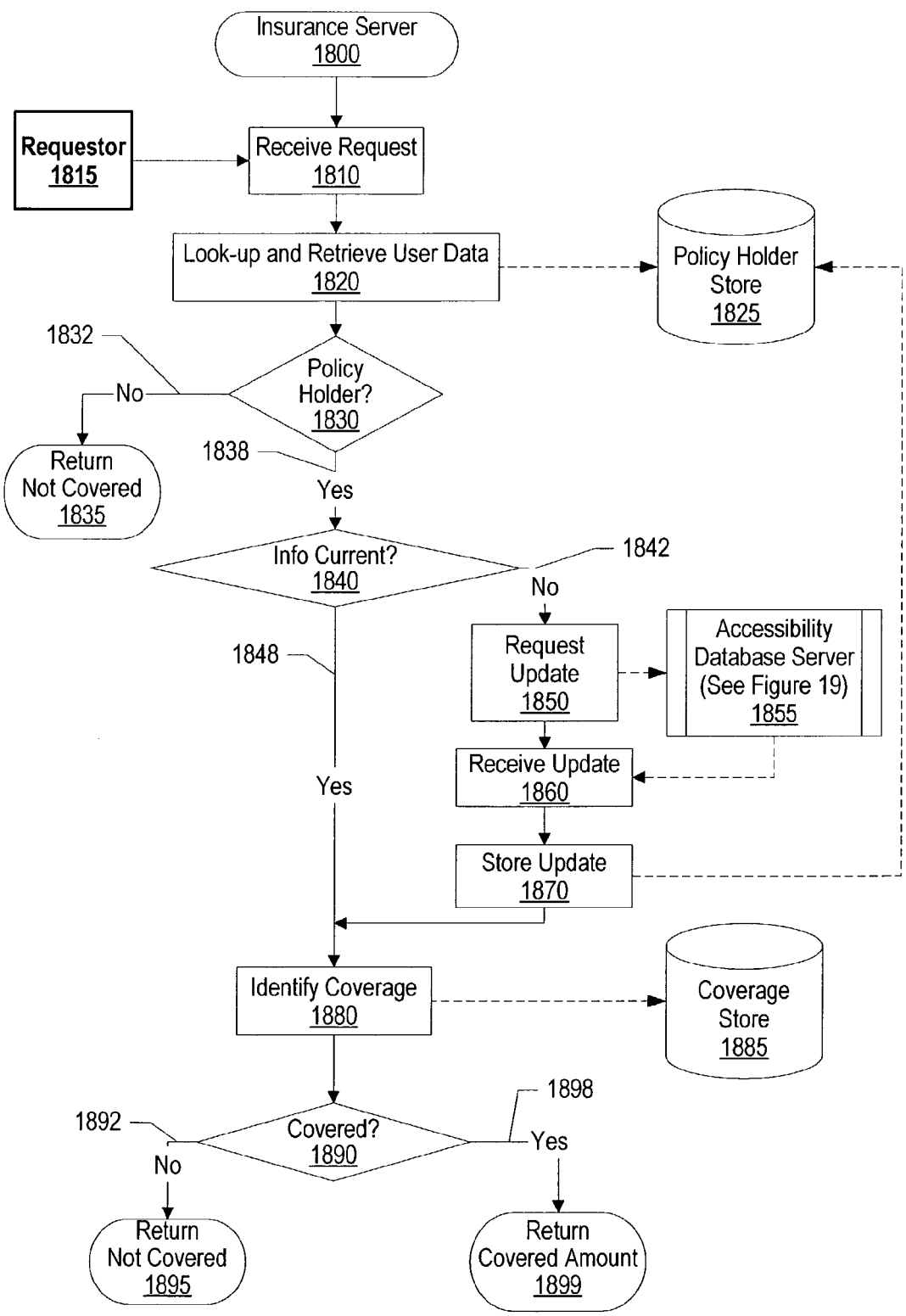
FIG. 18 is a flowchart showing steps taken in an insurance server receiving a coverage request and processing the coverage request.

FIG. 18 is a flowchart showing steps taken in an insurance server receiving a coverage request and processing the coverage request. The insurance server validates policy holder coverage, manages payments, and tracks user deductibles.

Processing commences at 1800, whereupon processing receives a coverage request which includes a user identifier from requestor 1815 (step 1810). Requestor 1815 may be an accounting server or a service provider in which a user corresponding to the user identifier is accessing. For example, the user may be requesting a wheelchair at an airport and the airport wheelchair service server is requesting coverage information from the user's insurance company.

Processing looks up the user identifier along with the user's accessibility data located in policy holder store 1825. In one embodiment, due to privacy concerns, processing does not store user information on a non-volatile storage area but rather receives the user information in the request. The user's accessibility data includes the user's accessibility privileges, claims paid to date, and the last time that the user's accessibility data was updated (see FIG. 10 and corresponding text for further details regarding insurance record fields). Policy holder store 1825 may be stored on a non-volatile storage area, such as a computer hard drive.

A determination is made as to whether the user corresponding to the user identifier is a policy holder (decision 1830). If the user is not a policy holder, decision 1830 branches to "No" branch 1832 whereupon "Not Covered" is returned to requestor 1815 at 1835. On the other hand, if the user is a policy holder with the insurance server, decision 1830 branches to "Yes" branch 1838 whereupon a determination is made as to whether the user's accessibility record has been recently updated using an accessibility database (decision 1840). The insurance server makes this determination by analyzing the date at which the accessibility data update occurred. For example, if the insurance server's policy is to update a user's insurance record every quarter and the user's insurance record has not been updated for six months, the insurance server updates the user's record the next time a requestor requests information corresponding to the user.

If the user's insurance record is current, decision 1840 branches to "Yes" branch 1848, bypassing insurance record updating steps. On the other hand, if the user's insurance record is not current, decision 1840 branches to "No" branch 1842 whereupon the insurance server sends an update request to an accessibility database at step 1850. The accessibility database analyzes the request, validates the insurance server's access permissions, and sends a response (pre-defined process block 1855, see FIG. 19 and corresponding text for further details regarding accessibility database processing). Processing receives the accessibility database response which includes current accessibility data at step 1860. Processing stores the current accessibility data in the user's insurance record located in policy holder store 1825 at step 1870. In one embodiment, due to privacy concerns, processing does not store user information on a non-volatile storage area but rather discards the information once processing identifies a user's accessibility privileges.

Processing identifies user coverage using the user's accessibility data along with the user's policy information located in coverage store 1885. For example, the user may have accessibility data that allows him to use a wheelchair and the user's insurance policy covers the cost of using a wheelchair. Coverage store 1885 may be stored on a non-volatile storage area, such as a computer hard drive.

A determination is made as to whether the user has insurance coverage corresponding to the request (decision 1890). If the user does not have insurance coverage corresponding to the request, decision 1890 branches to "No" branch 1892 whereupon "Not Covered" is returned to requestor 1815 at 1895. On the other hand, if the user does have insurance coverage corresponding to the request, decision 1890 branches to "Yes" branch 1898 whereupon the amount of coverage is returned to requestor 1815 at 1899. Using the example described above, the user may be covered for 80% of the cost of using a wheelchair.

In one embodiment, processing receives electronic bills from service providers or accounting servers and the insurance server electronically pays the bill. In another embodiment, a service provider or accounting server automatically debits the insurance server's account for faster payment.

Figure 19:
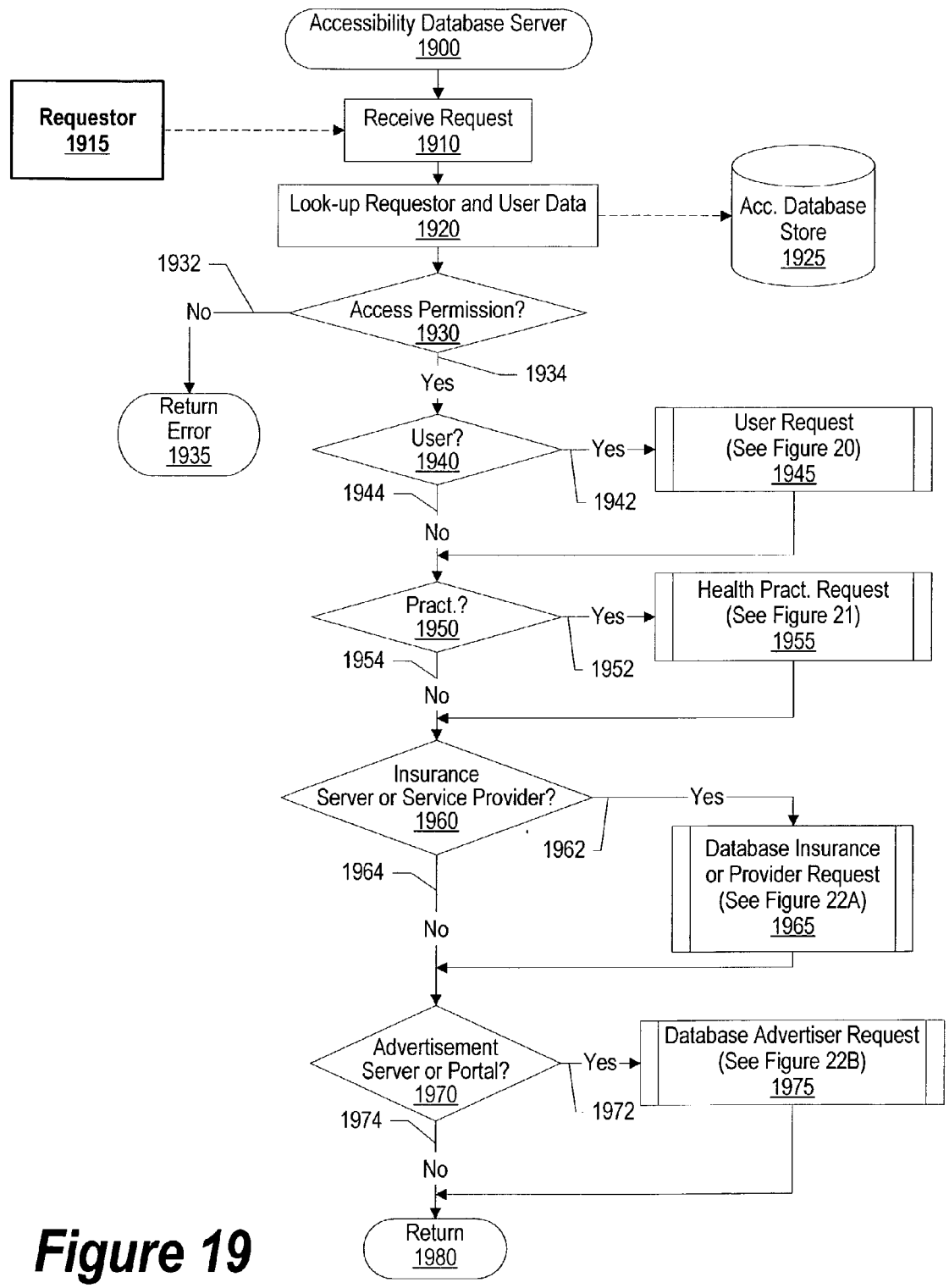
FIG. 19 is a flowchart showing steps taken in an accessibility database server receiving a request and processing the request.

FIG. 19 is a flowchart showing steps taken in an accessibility database server receiving a request and processing the request. The request is sent from a requestor, such as requestor 1915, wherein the request includes a user identifier corresponding to a user. Processing commences at 1900, whereupon processing receives the request from requestor 1915 at step 1919. Processing looks-up the requestor along with user data corresponding to the user identifier located in accessibility database store 1925. Accessibility database store 1925 may be stored on a non-volatile storage area, such as a computer hard drive.

A determination is made as to whether the requestor has access permission corresponding to his particular request (decision 1930). For example, the requestor may be an insurance server and processing determines whether the insurance server has access permissions corresponding to the user data by checking the insurance server's identifier with the user data (see FIGS. 9A, 9B, and corresponding text for further details regarding access permissions). If requestor 1915 is not permitted access corresponding to the request, decision 1930 branches to "No" branch 1932 whereupon an error is returned to requestor 1915 at 1935.

On the other hand, if requestor 1915 is permitted access, decision 1930 branches to "Yes" branch 1934 whereupon a determination is made as to whether requestor 1915 is a user (decision 1940). If requestor 1915 is a user, decision 1940 branches to "Yes" branch 1942 whereupon the user's request is processed (pre-defined process block 1945, see FIG. 20 and corresponding text for further details regarding user request processing). On the other hand, if requestor 1915 is not a user, decision 1940 branches to "No" branch 1944.

A determination is made as to whether requestor 1915 is a healthcare practitioner server (decision 1950). If requestor 1915 is a healthcare practitioner server, decision 1950 branches to "Yes" branch 1952 whereupon the healthcare practitioner server's request is processed (pre-defined process block 1955, see FIG. 21 and corresponding text for further details regarding health practitioner request processing). On the other hand, if requestor 1915 is not a healthcare practitioner server, decision 1950 branches to "No" branch 1954.

A determination is made as to whether requestor 1915 is an insurance server or a service provider (decision 1960). If requestor 1915 is an insurance server or a service provider, decision 1960 branches to "Yes" branch 1962 whereupon the insurance server or service provider request is processed (pre-defined process block 1965, see FIG. 22A and corresponding text for further details regarding insurance server and service provider request processing). On the other hand, if requestor 1915 is not an insurance server or a service provider, decision 1960 branches to "No" branch 1964.

A determination is made as to whether requestor 1915 is an advertisement server or portal (decision 1970). If requestor 1915 is an advertisement server or portal, decision 1970 branches to "Yes" branch 1972 whereupon the request is processed (pre-defined process block 1955, see FIG. 22B and corresponding text for further details regarding advertisement server or portal request processing). On the other hand, if requestor 1915 is not an advertisement server or portal, decision 1970 branches to "No" branch 1974. Processing returns at 1980.

Figure 20:
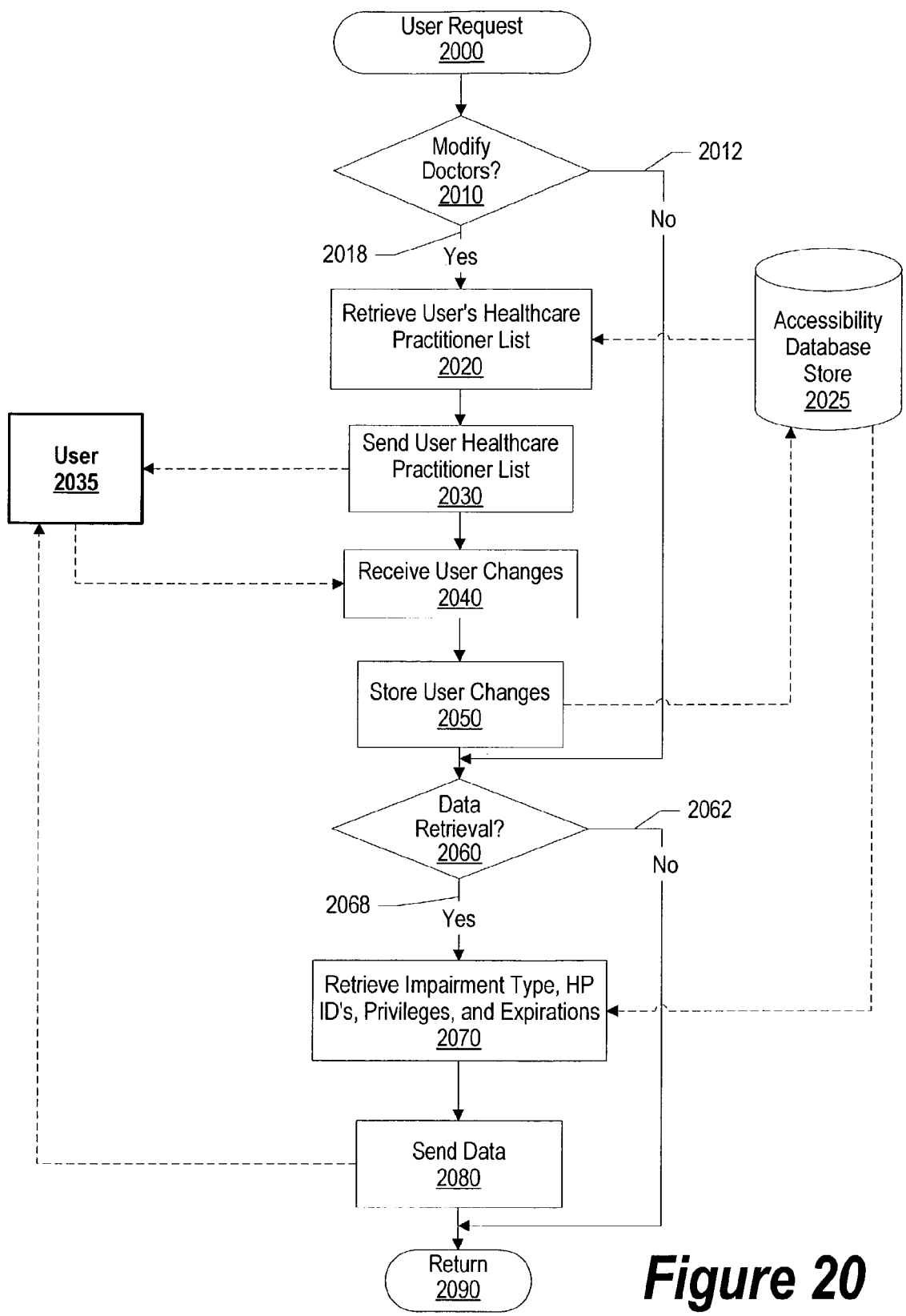
FIG. 20 is a flowchart showing steps taken in an accessibility database processing a user request.

FIG. 20 is a flowchart showing steps taken in an accessibility database processing a user request. Processing commences at 2000, whereupon a determination is made as to whether the user wishes to modify doctors in the user's database record (decision 2010). For example, the user may have recently broken his leg, and the user wishes to enter a healthcare practitioner identifier corresponding to the doctor who is administering care of his broken leg.

If the user does not wish to modify healthcare practitioner information, decision 2010 branches to "No" branch 2012, bypassing healthcare practitioner modifications steps. On the other hand, if the user wishes to modify healthcare practitioner information in his database record, decision 2010 branches to "Yes" branch 2018, whereupon processing retrieves the user's corresponding doctor list information located in accessibility databases store 2025 (step 2020). Database store 2025 may be stored on a nonvolatile storage area, such as a computer hard drive.

Processing sends the healthcare practitioner identifier list to user 2035 at step 2030. User 2035 analyzes the healthcare practitioner identifier list, and sends healthcare practitioner identifier information which processing receives at step 2040. Using the example described above, user 2035 sends information corresponding to the doctor that is administering care for the user's broken leg. Processing stores the user's changes in database store 2025 at step 2050.

A determination is made as to whether the user wishes to retrieve user data (decision 2060). For example, the user may wish to update his pervasive computing device with recent user data information. If the user does not wish to retrieve user data, decision 2060 branches to "No" branch 2062, bypassing data retrieval and sending steps, and processing returns at 2090. On the other hand, if the user wishes to retrieve user data information, decision 2060 branches to "Yes" branch 2068 whereupon processing retrieves user data from database store 2025 at step 2070 corresponding to the requestor's access permissions (see FIG. 9A and corresponding text for further details regarding access permissions). Processing sends the user data to user 2035 at step 2080, and processing returns at 2090.

Figure 21:
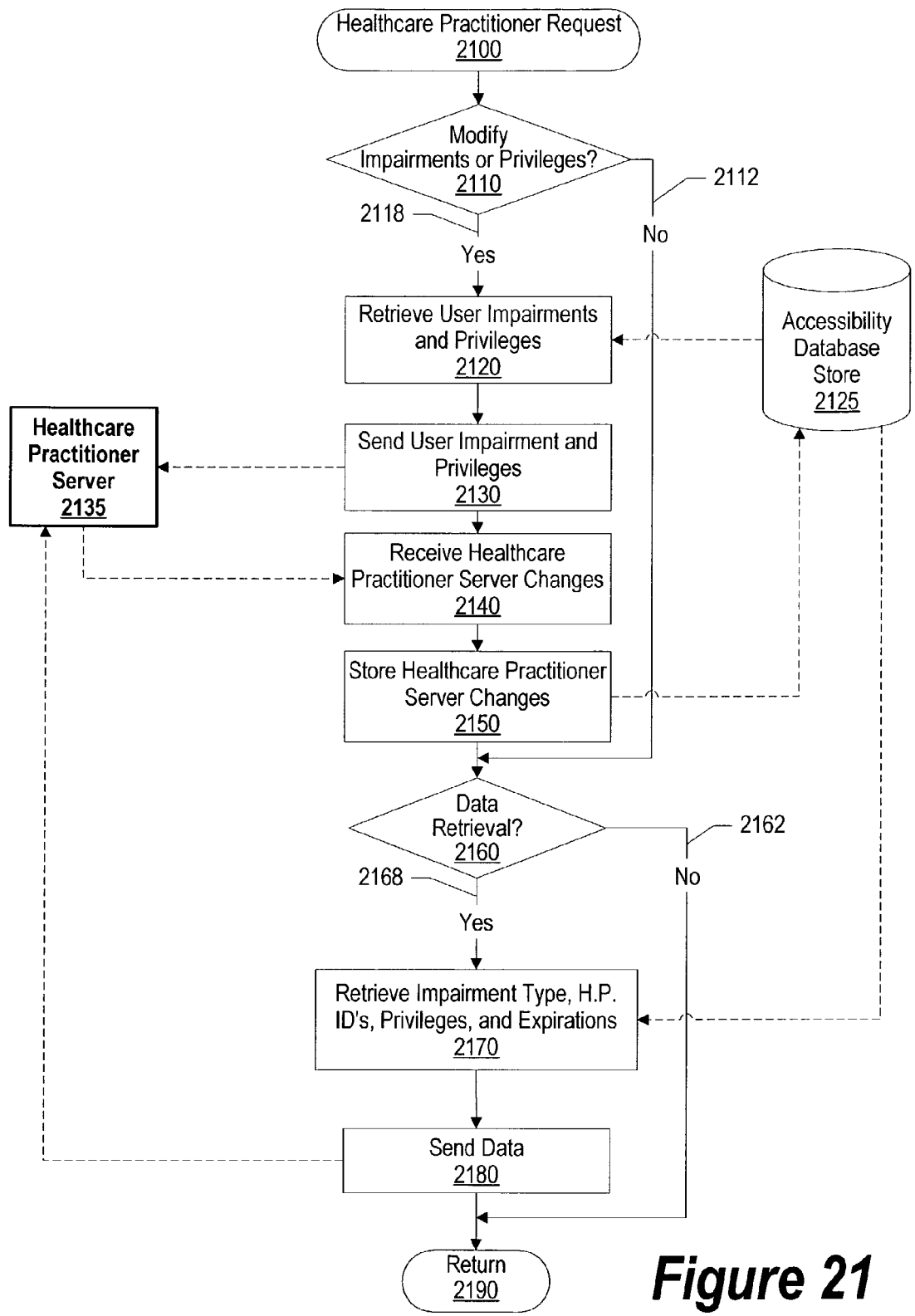
FIG. 21 is a flowchart showing steps taken in an accessibility database processing a healthcare practitioner server request.

FIG. 21 is a flowchart showing steps taken in an accessibility database processing a healthcare practitioner server request. For example, a user's doctor may access the accessibility database to enter accessibility type information corresponding to the user. Processing commences at 2100, whereupon a determination is made as to whether the healthcare practitioner server wishes to enter accessibility type or accessibility privileges corresponding to the user (decision 2110). A healthcare practitioner server is able to enter data into a user's database record as well as retrieve information from the user's database record (see FIG. 9A and corresponding text for further details regarding healthcare practitioner server access permissions).

If the healthcare practitioner server does not wish to enter user data, decision 2110 branches to "No" branch 2112 bypassing data entry steps. On the other hand, if the healthcare practitioner server wishes to enter data, decision 2110 branches to "Yes" branch 2118 whereupon processing retrieves the user's accessibility types and accessibility privileges from accessibility database store 2125 at step 2120. Accessibility database store 2125 may be stored on a non-volatile storage area, such as a computer hard drive. Processing sends the user's accessibility types and accessibility privileges to healthcare practitioner server 2135 at step 2130. Healthcare practitioner server 2135 analyzes the user data, and sends changes to the accessibility database server. Processing receives the changes at step 2140, and stores the changes in accessibility database store 2125 (step 2150).

A determination is made as to whether the healthcare practitioner server wishes to retrieve user database record information (decision 2160). If the healthcare practitioner server does not wish to retrieve user database record information, decision 2160 branches to "No" branch 2162 bypassing database retrieval steps. On the other hand, if the healthcare practitioner server wishes to retrieve database record information, decision 2160 branches to "Yes" branch 2168 whereupon processing retrieves database record information from accessibility database store 2125 (step 2170), and sends the database record information to healthcare practitioner server 2135 at step 2180. Processing returns at 2190.

Figure 22A:
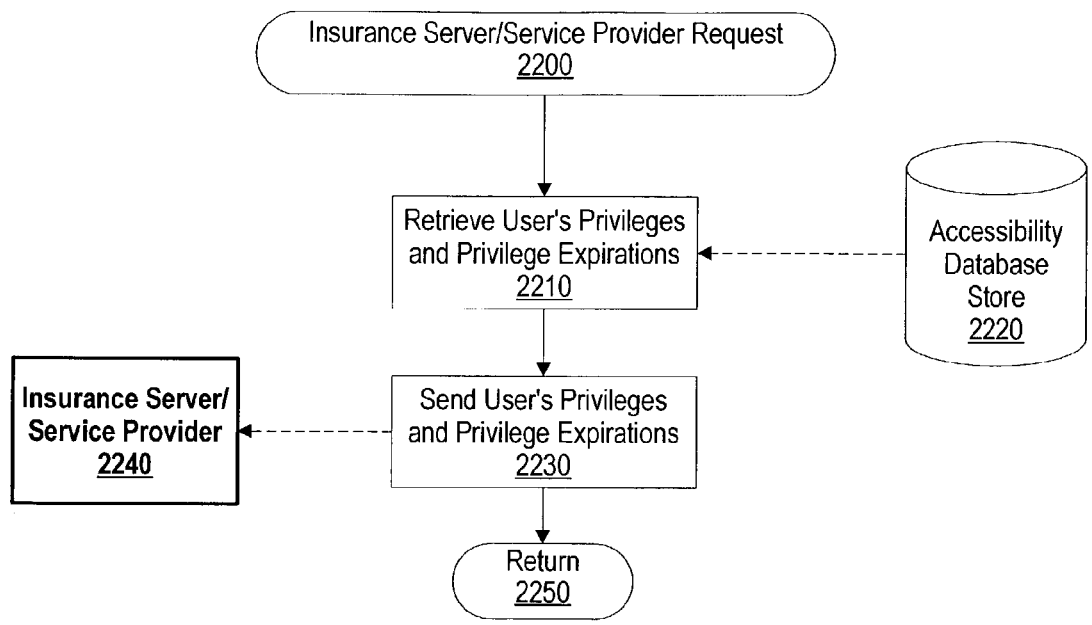
FIG. 22A is a flowchart showing steps taken in an accessibility database server processing an insurance server or a service provider request.

FIG. 22A is a flowchart showing steps taken in an accessibility database server processing an insurance server or a service provider request. The request includes a requestor identifier and a user identifier. The requestor identifier identifies the requestor, such as an insurance server, and the user identifier corresponds to the user data that the requestor is requesting. Processing previously used the requestor identifier to identify that the requestor is either an insurance server or a service provider (see FIG. 19 and corresponding text for further details regarding access permissions).

Processing commences at 2200, whereupon processing retrieves user data corresponding to the user identifier from accessibility database store 2220. Accessibility database store 2220 may be stored on a non-volatile storage area, such as a computer hard drive. Since processing previously identified the requestor as an insurance server or a service provider, processing retrieves user information that the requestor is permitted access, such as accessibility privileges and privilege expiration dates. An insurance server or a service provider may not be authorized to access other data record information or enter data record information for a particular user (see FIG. 9A and corresponding text for further details regarding access permissions).

Processing sends the accessibility privileges and privilege expiration dates to insurance server/service provider 2240 at step 2230, and processing returns at 2250.

Figure 22B:
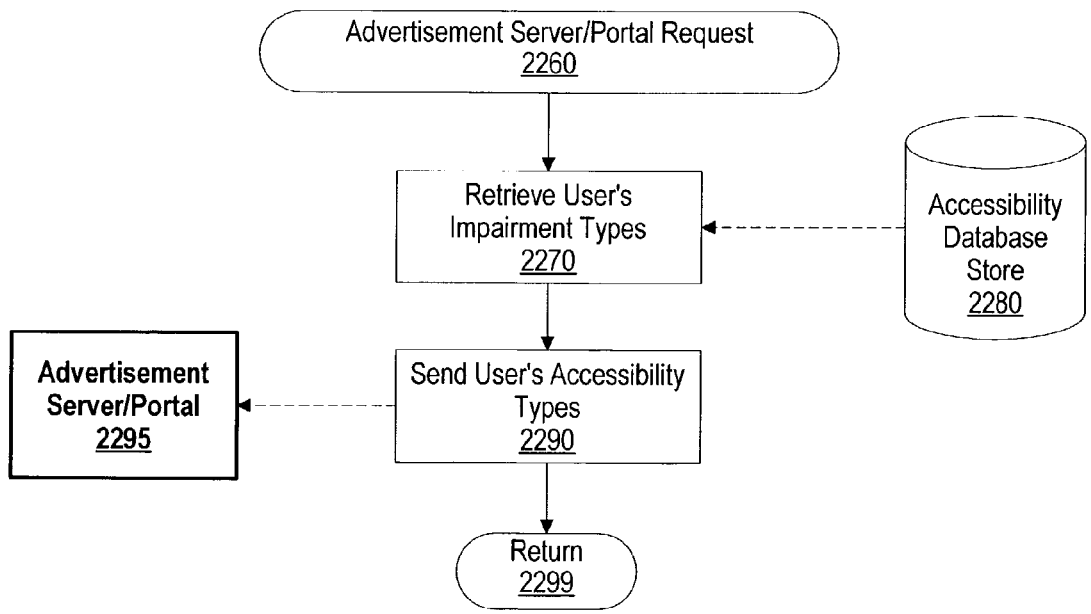
FIG. 22B is a flowchart showing steps taken in an accessibility database server processing an advertisement server or a portal server request.

FIG. 22B is a flowchart showing steps taken in an accessibility database server processing an advertisement server or a portal request. The request includes a requestor identifier and a user identifier. The requestor identifier identifies the requestor, such as an advertising server, and the user identifier identifies the user that is requesting a particular service. Processing used the requestor identifier and the user identifier to determine the requestor's access permissions (see FIG. 19 and corresponding text for further details regarding access permissions).

Processing commences at 2260, whereupon processing retrieves user information corresponding to the user identifier from accessibility database store 2280 (step 2270). Accessibility database store 2280 may be stored on a non-volatile storage area, such as a computer hard drive. Since processing previously identified the requestor as an advertisement server or portal, processing retrieves user accessibility type information from the accessibility database. For example, the user's corresponding accessibility type may be "blind" which notifies the advertisement server to send a "spoken" advertisement to the user. An advertisement server and a portal may not be authorized to access other data record information or enter data record information for a particular user (see FIG. 9A and corresponding text for further details regarding access permissions).

Processing sends the user's accessibility types to advertisement server/portal 2295 at step 2290, and processing returns at 2299.

FIG. 23 is a flowchart showing steps taken in a service provider receiving a request from a user's pervasive computing device, processing the request, and authorizing the user. Processing commences at 2300, whereupon processing receives a request from pervasive computing device 2310 at step 2305. For example, the user may wish to access a service, such as a handicap parking garage. During the request, the user may be required to enter information to validate his identity. For example, the user may be required to enter a "PIN" number on a keypad.

A determination is made as to whether the user has entered information to validate his identity (decision 2315). If the user did not enter information to validate his identity, decision 2315 branches to "No" branch 2317 whereupon processing returns and error at 2319. On the other hand if the user enters information that validated his identity, decision 2315 branches to "Yes" branch 2319 whereupon processing looks up user information in user data store 2325 (step 2320). User data store 2325 is the service provider's local storage area in which the service provider stores information corresponding to various users. Using the example described above, the parking garage server stores user information corresponding to customers that have previously used the parking garage service. In one embodiment, due to privacy concerns, processing does not store user information on a non-volatile storage area but rather receives the user information in the request.

A determination is made as to whether processing matches the user identifier with a stored user identifier located in user data store 2325 (decision 2330). If processing identifies the user identifier in user data store 2325, decision 2330 branches to "Yes" branch 2334, bypassing accessibility privileges requesting steps.

On the other hand, if processing did not identify the user, decision 2330 branches to "No" branch 2332 whereupon processing sends a request to an accessibility database to request accessibility privileges corresponding to the user identifier (step 2335). The accessibility database server receives the request, retrieves accessibility data corresponding to the request, and sends a response to the service provider server (predefined process block 2340, see FIG. 19 and corresponding text for further details regarding accessibility database request processing). Processing receives accessibility privileges information from the accessibility database server at step 2345.

A determination is made as to whether the user is authorized for the service provider's particular service (decision 2350). Using the example described above, processing determines whether the user is authorized for handicap parking. If the user is not authorized for the service provider's corresponding service, decision 2350 branches to "No" branch 2352 whereupon and error is returned to the user at 2355. On the other hand if the user is authorized to receive the service provider's corresponding service, decision 2350 branches to "Yes" branch 2354 whereupon the user's information is stored in user data store 2325 at step 2360. Processing stores the user's information for later retrieval when the user wishes to access the service provider's service at a later time. In one embodiment, due to privacy concerns, processing does not store user information on a non-volatile storage area but rather discards the information once processing identifies a user's accessibility privileges.

A determination is made as to whether the service provider should charge the user for using the service provider's service (decision 2365). Using the example described above, the parking garage server may have a free day in which all users receive free parking. In this example, the parking garage server does not charge the user for the service. If the service provider chooses not to charge the user, decision 2365 branches to "No" branch 2367 bypassing transaction steps.

On the other hand, if the service provider chooses to charge the user, decision 2365 branches to "Yes" branch 2369 whereupon processing invokes transaction steps (predefined process block 2370, see FIG. 24 in corresponding text for further details). Transaction processing includes checking with the user's corresponding insurance provider server determine coverage information.

A determination is made as to whether the service is paid for by the user or the user's insurance server (decision 2380). If the service fee is not paid in full, decision 2380 branches to "No" branch 2382 whereupon processing returns "Not Paid" at 2385. On the other hand, if the user is authorized, decision 2380 branches to "Yes" branch 2384.

Processing authorizes the user by sending an authorization to pervasive computing device 2310 (step 2390), and processing returns at 2395.

FIG. 24 is a flowchart showing steps taken in a service provider server processing a user transaction. The user transaction results in the user obtaining access to a particular service. For example, the user may have requested, and obtained authorization to park at a handicap parking garage and the service provider (i.e. parking garage server) is charging the user a service fee (see FIG. 23 and corresponding text for further details regarding user access validation). Processing commences at 2400, whereupon, processing requests insurance information from the user's pervasive computing device, such as pervasive computing device 2415. Processing receives insurance information from pervasive computing device 2415 at step 2420. The insurance information may include the insurance provider's name, an insurance provider identifier, coverage type information, and the user's policy number.

A determination is made as to whether the user's insurance pays for at least a portion of the requested service (decision 2430). Using the example described above, processing determines whether the user's insurance pays for all, or a portion of, handicap parking charges. In one embodiment, processing may not know the user's coverage information and bill the insurance company directly. If processing determined that the user's insurance does not cover the service, decision 2430 branches to "No" branch 2438 bypassing insurance coverage checking steps.

On the other hand, if the user's insurance server pays for at least a portion of the service, decision 2430 branches to "Yes" branch 2432 whereupon processing validates the user's insurance coverage at step 2440. The insurance company receives the request, analyzes the request, and sends a response back to the service provider server (pre-defined process block 2445, see FIG. 18 and corresponding text for further details regarding insurance request processing).

Processing receives the insurance server's response at step 2450. A determination is made as to whether the insurance server agrees to pay the service fee in full (decision 2460). Using the example described above, the insurance server may pay only half of the handicap parking garage fee. If the insurance server agrees to pay the service fee in full, decision 2460 branches to "Yes" branch 2468, bypassing user billing steps. On the other hand, if the insurance server does not agree to pay the service fee in full, decision 2460 branches to "No" branch 2462. Processing sends a request to pervasive computing device 2415 to pay for any remaining service fee (step 2470). Processing receives a response from the pervasive computing device 2415 at step 2480 which includes payment information.

A determination is made as to whether the service fee has been paid in full (decision 2490). If the service is not paid in full, decision 2490 branches to "No" branch 2498 whereupon "Not Authorized" is returned at 2499. On the other hand, if the service is paid in full, decision 2490 branches to "Yes" branch 2492 whereupon "Authorized" is returned at 2495.

Figure 25:
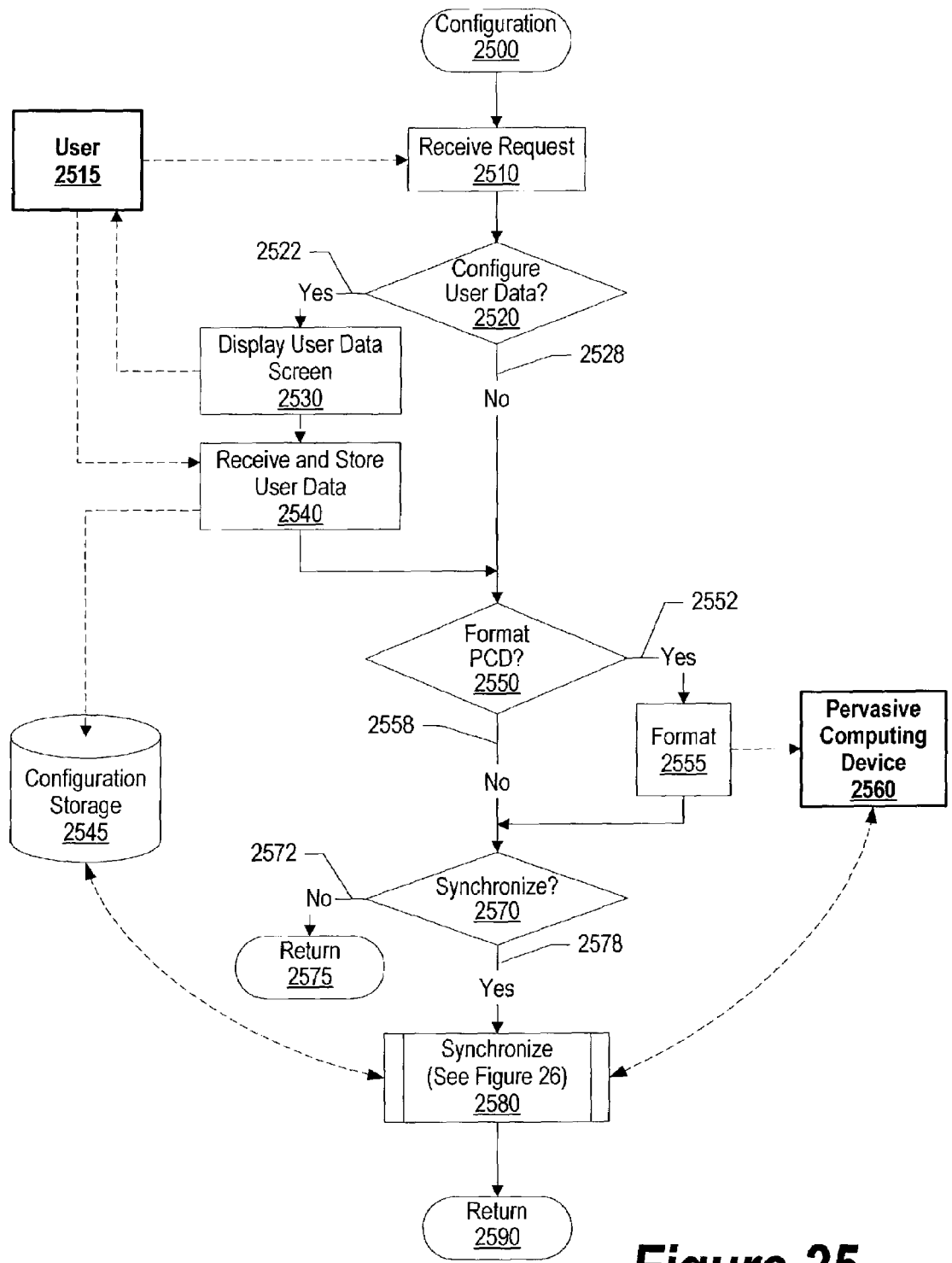
FIG. 25 is a flowchart showing steps taken in a user using a client to configure a pervasive computing device.

FIG. 25 is a flowchart showing steps taken in a user using a client to configure a pervasive computing device. Configuration processing commences at 2500, whereupon processing receives a request from user 2515 at step 2510. A determination is made as to whether the user wishes to configure user data information (decision 2520). If the user does not wish to configure user data information, decision 2520 branches to "No" branch 2528, bypassing preference display and retrieving steps. On the other hand, if the user wishes to configure user data information, decision 2520 branches to "Yes" branch 2522 whereupon processing displays a user data screen to user 2515. The user data screen is displayed on a display and includes existing user data settings.

The user data screen includes user identifier information, content presentation preferences, and billing information. The billing information is used when a fee is charged for a particular service, such as bus fare or content transcoding (see FIG. 8B and corresponding text for further details regarding user data screen properties). Processing receives user data from user 2515, and stores it in configuration store 2545 (step 2540). Configuration store 2545 may be stored on a non-volatile storage area, such as a computer hard drive.

A determination is made as to whether the user wishes to format his pervasive computing device, such as pervasive computing device 2560 (decision 2550). If the user wishes to format pervasive computing device 2560, decision 2550 branches to "Yes" branch 2552 whereupon processing formats pervasive computing device 2560 by sending a format command to pervasive computing device 2560 (step 2555). On the other hand, if the user does not wish to format pervasive computing device 2560, decision 2550 branches to "No" branch 2558, bypassing formatting steps.

A determination is made as to whether the user wishes to synchronize the client with pervasive computing device 2560 (decision 2570). For example, the user may have recent information on the client and wish to download the recent information into pervasive computing device 2560. If the user does not wish to synchronize his pervasive computing device 2560, decision 2570 branches to "No" branch 2572 whereupon processing returns at 2575.

Figure 26:
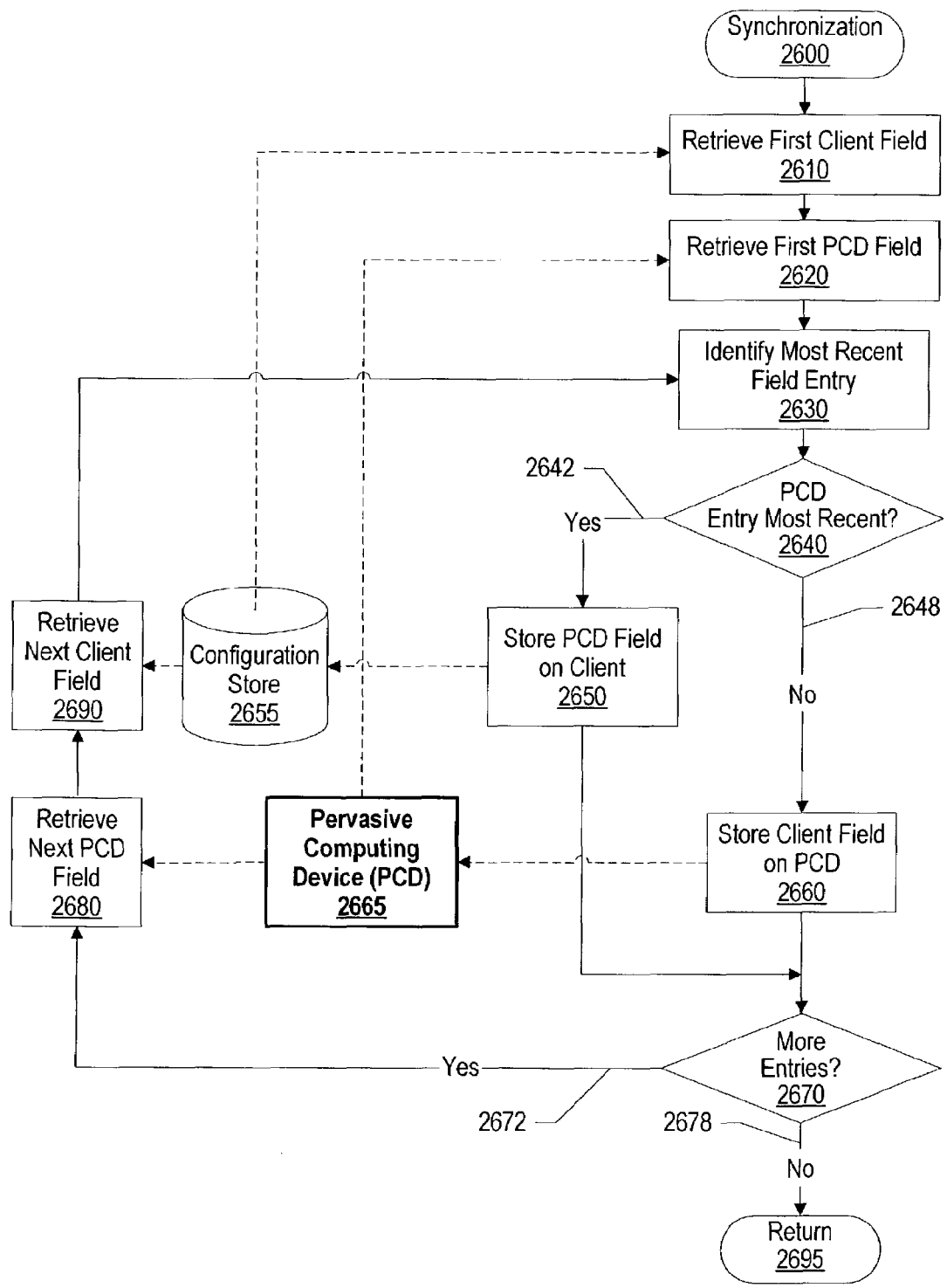
FIG. 26 is a flowchart showing steps taken in a client synchronizing with a pervasive computing device.

On the other hand, if the user wishes to synchronize the client with pervasive computing device 2560, decision 2570 branches to "Yes" branch 2578 whereupon processing synchronizes user data included in configuration store 2545 with pervasive computing device 2565 (pre-defined process block 2580, see FIG. 26 and corresponding text for further details regarding synchronization). Processing returns at 2590.

FIG. 26 is a flowchart showing steps taken in a client synchronizing with a pervasive computing device, such as pervasive computing device 2665. Synchronization processing commences at 2600, whereupon processing retrieves a first client field from configuration store 2655. For example, the first client field may be "Zoom" and the value may be "150%". Configuration store may be stored on a non-volatile storage area, such as a computer hard drive. Processing retrieves a first pervasive computing device field from pervasive computing device 2665 at step 2620. Using the example described above, the first pervasive computing device field from pervasive computing device 2665 is zoom and its value is "200%". Processing identifies which entry (i.e. the client's or the pervasive computing device's) is the most recent by comparing the time at which each field was entered.

A determination is made as to whether the pervasive computing device entry is the more recent entry (decision 2640). If the pervasive computing device entry is more recent, decision 2640 branches to "Yes" branch 2642 whereupon processing stores the pervasive computing device entry in configuration store 2655 (step 2650). On the other hand, if the client entry is more recent, decision 2640 branches to "No" branch 2648 whereupon processing stores the client entry on pervasive computing device 2665 (step 2660).

A determination is made as to whether there are more entry fields to synchronize (decision 2670). If there are more entries to synchronize, decision 2670 branches to "Yes" branch 2672 which loops back to retrieve the next pervasive computing device entry (step 2680), retrieve the next client field entry (step 2690), and process the two entries. This looping continues until there are no more entries to process, at which point decision 2670 branches to "No" branch 2678 whereupon processing returns at 2695.

Figure 27:
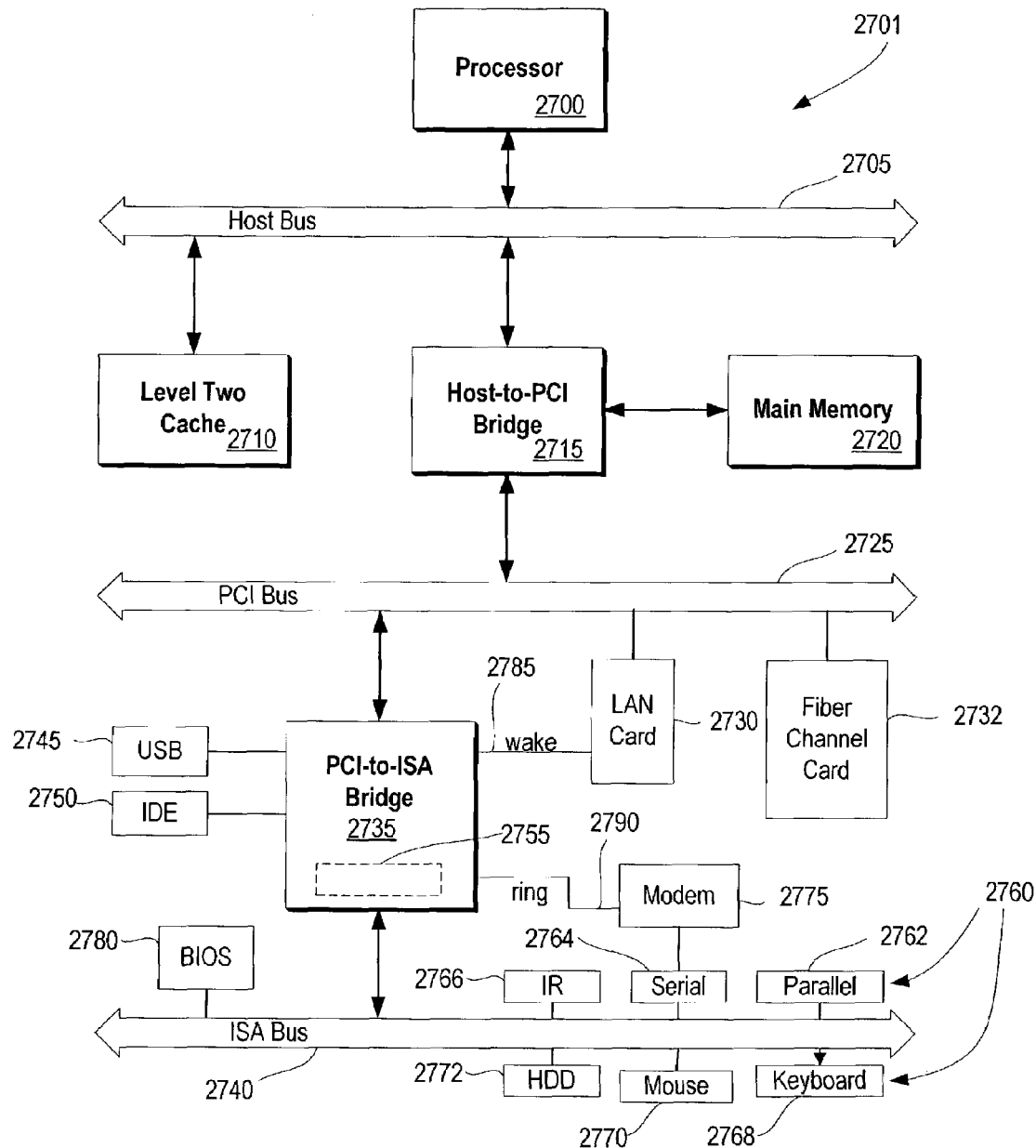
FIG. 27 is a block diagram of an information handling system capable of implementing the present invention.

FIG. 27 illustrates information handling system 2701 which is a simplified example of a computer system capable of performing the invention described herein. Computer system 2701 includes processor 2700 which is coupled to host bus 2705. A level two (L2) cache memory 2710 is also coupled to the host bus 2705. Host-to-PCI bridge 2715 is coupled to main memory 2720, includes cache memory and main memory control functions, and provides bus control to handle transfers among PCI bus 2725, processor 2700, L2 cache 2710, main memory 2720, and host bus 2705. PCI bus 2725 provides an interface for a variety of devices including, for example, LAN card 2730. PCI-to-ISA bridge 2735 provides bus control to handle transfers between PCI bus 2725 and ISA bus 2740, universal serial bus (USB) functionality 2745, IDE device functionality 2750, power management functionality 2755, and can include other functional elements not shown, such as a real-time clock (RTC), DMA control, interrupt support, and system management bus support. Peripheral devices and input/output (I/O) devices can be attached to various interfaces 2760 (e.g., parallel interface 2762, serial interface 2764, infrared (IR) interface 2766, keyboard interface 2768, mouse interface 2770, and fixed disk (HDD) 2772) coupled to ISA bus 2740. Alternatively, many I/O devices can be accommodated by a super I/O controller (not shown) attached to ISA bus 2740.

BIOS 2780 is coupled to ISA bus 2740, and incorporates the necessary processor executable code for a variety of low-level system functions and system boot functions. BIOS 2780 can be stored in any computer readable medium, including magnetic storage media, optical storage media, flash memory, random access memory, read only memory, and communications media conveying signals encoding the instructions (e.g., signals from a network). In order to attach computer system 2701 to another computer system to copy files over a network, LAN card 2730 is coupled to PCI bus 2725 and to PCI-to-ISA bridge 2735. Similarly, to connect computer system 2701 to an ISP to connect to the Internet using a telephone line connection, modem 2775 is connected to serial port 2764 and PCI-to-ISA Bridge 2735.

While the computer system described in FIG. 27 is capable of executing the invention described herein, this computer system is simply one example of a computer system. Those skilled in the art will appreciate that many other computer system designs are capable of performing the invention described herein.

One of the preferred implementations of the invention is an application, namely, a set of instructions (program code) in a code module which may, for example, be resident in the random access memory of the computer. Until required by the computer, the set of instructions may be stored in another computer memory, for example, on a hard disk drive, or in removable storage such as an optical disk (for eventual use in a CD ROM) or floppy disk (for eventual use in a floppy disk drive), or downloaded via the Internet or other computer network. Thus, the present invention may be implemented as a computer program product for use in a computer. In addition, although the various methods described are conveniently implemented in a general purpose computer selectively activated or reconfigured by software, one of ordinary skill in the art would also recognize that such methods may be carried out in hardware, in firmware, or in more specialized apparatus constructed to perform the required method steps.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those with skill in the art that if a specific number of an introduced claim element is intended, such intent will be explicitly recited in the claim, and in the absence of such recitation no such limitation is present. For a non-limiting example, as an aid to understanding, the following appended claims contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to inventions containing only one such element, even when the same claim includes the introductory phrases "one or more" or "at least one" and indefinite articles such as "a" or "an"; the same holds true for the use in the claims of definite articles.

What is claimed is:

1. A computer-implemented method of managing an accessibility database, wherein the accessibility database includes accessibility data corresponding to a plurality of users, said method comprising:

receiving an accessibility record request from a requestor, wherein the accessibility record request includes a user identifier and a requestor identifier, the requestor identifier corresponding to the requestor;

retrieving a database record corresponding to the user identifier;

identifying access permissions based upon the requestor identifier;

providing access to accessibility data included in the database record based upon the access permissions;

detecting that the accessibility record request corresponds to writing input data in the database record;

determining, in response to the detecting, whether to allow the requestor to write the input data into the database record based upon the requestor identifier;

receiving the input data from the requestor in response to determining to allow the requestor to write the input data into the database record; and storing the received input data in the database record.

2. The method as described in claim 1 wherein the requestor is selected from the group consisting of a user, a healthcare practitioner server, an insurance server, a transcoding proxy server, a portal server, a web server, an advertisement server, and a service provider.

3. The method as described in claim 1 wherein the accessibility data includes one or more fields and wherein at least one of the fields is selected from the group consisting of an accessibility type, a healthcare practitioner identifier, an accessibility privilege, and a privilege expiration.

4. The method as described in claim 1 wherein the requestor is a healthcare practitioner server, the method further comprising:

authorizing the healthcare practitioner to enter input data, wherein the input data is selected from the group consisting of an accessibility type, an accessibility privilege, and a privilege expiration;

receiving the input data from the healthcare practitioner server; and storing the input data in the database record.

5. The method as described in claim 1 wherein the requestor is a user that corresponds to the user identifier, the method further comprising:

authorizing the user to enter a healthcare practitioner identifier;

receiving the healthcare practitioner identifier from the user; and storing the healthcare practitioner identifier in the database record, the storing allowing a healthcare practitioner corresponding to the healthcare practitioner identifier to access the database record.

6. The method as described in claim 1 further comprising:

determining whether the requestor has access premissions corresponding to the accessibility record request; and denying access to the requestor based upon the determination.

7. An information handling system comprising:

one or more processors;

a memory accessible by the processors;

one or more nonvolatile storage devices accessible by the processors; and an accessibility database management tool to manage an accessibility database, the accessibility database management tool including:

means for receiving an accessibility record request from a requestor, wherein the accessibility record request includes a user identifier and a requestor identifier, the requestor identifier corresponding to the requestor;

means for retrieving a database record corresponding to the user identifier from one of the nonvolatile storage devices;

means for identifying access permissions based upon the requestor identifier;

means for providing access to accessibility data included in the database record based upon the access permissions;

means for detecting that the accessibility record request corresponds to writing input data in the database record;

means for determining, in response to the detecting, whether to allow the requestor to write the input data into the database record based upon the requestor identifier;

means for receiving the input data from the requestor in response to determining to allow the requestor to write the input data into the database record; and means for storing the received input data in the database record.

8. The information handling system as described in claim 7 wherein the requestor is selected from the group consisting of a user, a healthcare practitioner server, an insurance server, a transcoding proxy server, a portal server, a web server, an advertisement server, and a service provider.

9. The information handling system as described in claim 7 wherein the requestor is a healthcare practitioner server, the information handling system further comprising:

means for authorizing the healthcare practitioner server to enter input data, wherein the input data is selected from the group consisting of an accessibility type, an accessibility privilege, and a privilege expiration;

means for receiving the input data from the healthcare practitioner server; and means for storing the input data in the database record located on one of the nonvolatile storage devices.

10. The information handling system as described in claim 7 wherein the requestor is a user that corresponds to the user identifier, the information handling system further comprising:

means for authorizing the user to enter a healthcare practitioner identifier;

means for receiving the healthcare practitioner identifier from the user; and means for storing the healthcare practitioner identifier in the database record located on one of the nonvolatile storage devices, the storing allowing a healthcare practitioner corresponding to the healthcare practitioner identifier to access the database record.

11. The information handling system as described in claim 7 further comprising:

means for determining whether the requestor has access permissions corresponding to the accessibility record request; and means for denying the requestor based upon the determination.

12. A computer program product stored on a computer operable media for managing an accessibility database, said computer program product comprising:

means for receiving an accessibility record request from a requestor, wherein the accessibility record request includes a user identifier and a requestor identifier, the requestor identifier corresponding to the requestor;

means for retrieving a database record corresponding to the user identifier;

means for identifying access permissions based upon the requestor identifier;

means for providing access to accessibility data included in the database record based upon the access permissions;

means for detecting that the accessibility record request corresponds to writing input data in the database record;

means for determining, in response to the detecting, whether to allow the requestor to write the input data into the database record based upon the requestor identifier;

means for receiving the input data from the requestor in response to determining to allow the requestor to write the input data into the database record; and means for storing the received input data in the database record.

13. The computer program product as described in claim 12 wherein the requestor is selected from the group consisting of a user, a healthcare practitioner server, an insurance server, a transcoding proxy server, a portal server, a web server, an advertisement server, and a service provider.

14. The computer program product as described in claim 12 wherein the accessibility data includes one or more fields and wherein at least one of the fields is selected from the group consisting of an accessibility type, a healthcare practitioner identifier, an accessibility privilege, and a privilege expiration.

15. The computer program product as described in claim 12 wherein the requestor is a healthcare practitioner server, the computer program product further comprising:

means for authorizing the healthcare practitioner server to enter input data, wherein the input data is selected from the group consisting of an accessibility type, an accessibility privilege, and a privilege expiration;

means for receiving the input data from the healthcare practitioner server; and means for storing the input data in the database record.

16. The computer program product as described in claim 12 wherein the requestor is a user that corresponds to the user identifier, the computer program product further comprising:

means for authorizing the user to enter a healthcare practitioner identifier;

means for receiving the healthcare practitioner identifier from the user; and means for storing the healthcare practitioner identifier in the database record, the storing allowing a healthcare practitioner corresponding to the healthcare practitioner identifier to access the database record.

17. The computer program product as described in claim 12 further comprising:

means for determining whether the requestor has access permissions corresponding to the accessibility record request; and means for denying access to the requestor based upon the determination.

* * * * *